US010780060B2

(12) United States Patent
Unger et al.

(10) Patent No.: US 10,780,060 B2
(45) Date of Patent: Sep. 22, 2020

(54) ADJUSTING PARTICLE SIZE IN FLUOROCARBON NANOEMULSIONS

(71) Applicant: NuvOx Pharma LLC, Tucson, AZ (US)

(72) Inventors: Evan C. Unger, Tucson, AZ (US); Edmund Marinelli, Tucson, AZ (US)

(73) Assignee: NuvOx Pharma LLC, Tucson, AZ (US)

(*) Notice: Subject to any disclaimer, the term of this patent is extended or adjusted under 35 U.S.C. 154(b) by 0 days.

(21) Appl. No.: 15/749,758

(22) PCT Filed: Aug. 15, 2016

(86) PCT No.: PCT/US2016/047019
§ 371 (c)(1),
(2) Date: Feb. 1, 2018

(87) PCT Pub. No.: WO2017/031051
PCT Pub. Date: Feb. 23, 2017

(65) Prior Publication Data
US 2018/0221302 A1  Aug. 9, 2018

Related U.S. Application Data

(60) Provisional application No. 62/205,586, filed on Aug. 14, 2015.

(51) Int. Cl.
*A61K 31/02* (2006.01)
*B02C 19/18* (2006.01)
(Continued)

(52) U.S. Cl.
CPC .............. *A61K 31/02* (2013.01); *A61B 8/481* (2013.01); *A61K 9/1075* (2013.01); *A61M 5/178* (2013.01); *A61M 39/10* (2013.01); *B02C 19/18* (2013.01); *B06B 1/10* (2013.01); *A61K 9/0019* (2013.01); *A61M 2205/02* (2013.01); *A61M 2205/8275* (2013.01); *B82Y 40/00* (2013.01)

(58) Field of Classification Search
CPC ..... A61K 31/02; A61K 9/1075; A61M 39/10; A61M 5/178; A61B 8/481; B02C 19/18; B82Y 40/00
See application file for complete search history.

(56) References Cited

U.S. PATENT DOCUMENTS

| 4,497,829 A | 2/1985 | Sloviter | |
|---|---|---|---|
| 2010/0181218 A1* | 7/2010 | Beccaro | A61F 9/0017 206/365 |
| 2014/0004099 A1 | 1/2014 | Culp | |

FOREIGN PATENT DOCUMENTS

EP  0265082 A1  4/1988

OTHER PUBLICATIONS

Lattin, Ultrasound-Induced Phase Change for Targeted Gene and Drug Delivery, Dissertation, Department of Chamical Engineering, BYU, Doctor of Philosophy, (Year: 2012).*

(Continued)

*Primary Examiner* — Carlos A Azpuru
(74) *Attorney, Agent, or Firm* — Milstein Zhang & Wu LLC

(57) ABSTRACT

The invention provides devices and methods for adjusting particle size in nanoemulsions of fluorocarbons and perfluorocarbons (e.g., perfluoropentane and perfluorohexane) via sonication (e.g., ultrasonication).

6 Claims, 12 Drawing Sheets

(51) Int. Cl.
    *A61K 9/107*     (2006.01)
    *A61M 5/178*     (2006.01)
    *A61B 8/08*     (2006.01)
    *A61M 39/10*     (2006.01)
    *B06B 1/10*     (2006.01)
    *A61K 9/00*     (2006.01)
    *B82Y 40/00*     (2011.01)

(56) References Cited

OTHER PUBLICATIONS

Lattin, Ultrasound-Induced Phase Change for Targeted Gene and Drug Delivery, Dissertation, Department of Chemical Engineering, BYU, Doctor of Philosophy, pp. 1-154. (Year: 2012).*

EP 16837648.1-1114, Extended European Search Report, dated Mar. 7, 2019.

Bastien Arnal et al. "Inertial cavitation in theranostic nanoemulsions with simultaneous pulsed laser and low frequency ultrasound excitation" Proceedings of SPIE—The International Society for Optical Engineering 8943:89433E • Mar. 2014.

K. Astafyeva, et al. "Perfluorocarbon nanodroplets stabilized by fluorinated surfactants: characterization and potentiality as theranostic agents" J. Mater. Chem. B, vol. 3, No. 14, Jan. 1, 2015.

\* cited by examiner

ADJUSTING PARTICLE SIZE IN FLUOROCARBON NANOEMULSIONS

PRIORITY CLAIMS AND RELATED PATENT APPLICATIONS

This application is the U.S. national phase of and claims priority to PCT/US2016/047019, filed Aug. 15, 2016, which claims the benefit of priority to U.S. Provisional Application Ser. No. 62/205,586, filed on Aug. 14, 2015, the entire content of each of which is incorporated herein by reference in its entirety.

TECHNICAL FIELDS OF THE INVENTION

This invention relates to pharmaceutical compositions and methods of their preparation and therapeutic use. More particularly, the invention relates to methods and devices for adjusting particle size in nanoemulsions of fluorocarbons and perfluorocarbons (e.g., perfluoropentane and perfluorohexane) via mechanical vibration (e.g., sonication, in particular ultrasonication).

BACKGROUND OF THE INVENTION

Fluorocarbon (FC) and in particular perfluorocarbon (PFC) nanoemulsions have been disclosed as being useful in ultrasound imaging and as agents for oxygen delivery. PFC emulsions, such as dodecafluoropentane (DDFP) nanoemulsions in water, for example, comprise sub-micron sized droplets at room temperature. PFC nanoemulsions can be prepared by high-pressure homogenization, which is regarded as the method of choice.

Stability of FC/PFC nanoemulsions depends on numerous variables, amongst them the components, storage conditions, concentration, and container headspace. As will be discussed further herein, PFC nanoemulsions tend to exhibit growth in particle size over time. Large particle size (e.g. particles over 2 microns in size) may increase adverse events associated with vascular (e.g. IV) administration of the nanoemulsions. Instability of nanoemulsions is typically manifested by particle growth by the mechanism of Ostwald ripening, which, over time, may result in the emulsion having particle sizes exceeding the allowable specification, rendering them unsuitable for use and waste of the product or leading to safety risks if accidentally used.

Thus, a method is desired that can return the product to particle size parameters within specification. This would allow the use of the product for the expected application, reducing waste of the product at the manufacturing site and/or the marketplace.

SUMMARY OF THE INVENTION

The invention is based in part on the unexpected discovery of methods and devices that allow efficient and effective adjustment of particle size of FC/PFC nanoemulsions. Methods and devices of the invention can be employed at the manufacturing site or at the point of use employing widely available equipment. Sonication using ultrasound frequencies between about 10 KHz and about 1 MHz can be employed to reduce particle size of FC/PFC nanoemulsions to values comparable with and even equivalent to those FC/PFC nanoemulsions freshly prepared via high-pressure homogenization. Novel pre-filled syringes and injection systems can ensure particle size optimization and product safety and efficacy.

In one aspect, the invention generally relates to a method for reducing particle size of a perfluorocarbon nanoemulsion. The method includes applying mechanical vibration to the perfluorocarbon emulsion for a time duration sufficient to adjust the particle size of the perfluorocarbon emulsion to a pre-selected value. The perfluorocarbon nanoemulsion comprises a perfluorocarbon having from 4 to about 10 carbon atoms in length.

In certain embodiments, the perfluorocarbon emulsion is enclosed in a vial or pre-filled syringe.

In certain embodiments, the mechanical vibration comprises ultrasound. In certain embodiments, the ultrasound is characterized by a frequency from about 10 KHz to about 10 MHz. In certain embodiments, the perfluorocarbon is from about 4 to about 8 carbon atoms in length.

In certain embodiments of the method, the fluorocarbon is a perfluorocarbon. In certain embodiments, the perfluorocarbon comprises perfluoropentane, perfluorohexane, or both.

In certain embodiments of the method, the perfluorocarbon consists of perfluoropentane.

In certain embodiments of the method, the perfluorocarbon consists of perfluorohexane.

In another aspect, the invention generally relates to a pre-filled syringe of a fluorocarbon (e.g., perfluorocarbon) nanoemulsion, wherein the fluorocarbon is from about 4 to about 10 carbon atoms in length and the fluorocarbon nanoemulsion is from about 0.1% to 50% weight volume of the fluorocarbon.

In certain embodiments of the pre-filled syringe the fluorocarbon is a perfluorocarbon. In certain embodiments, the perfluorocarbon is from about 4 to about 8 carbon atoms in length.

In certain embodiments of the pre-filled syringe, the fluorocarbon is a perfluorocarbon. In certain embodiments, the perfluorocarbon comprises perfluoropentane, perfluorohexane, or both.

In certain embodiments of the pre-filled syringe, the perfluorocarbon consists of perfluoropentane.

In certain embodiments of the pre-filled syringe, the perfluorocarbon consists of perfluorohexane.

In certain embodiments of the pre-filled syringe, the syringe is made from a material comprising glass, plastic, or both.

In certain embodiments of the pre-filled syringe, the syringe is made from a glass material.

In certain embodiments of the pre-filled syringe, the syringe is made from a plastic material.

In certain embodiments of the pre-filled syringe, the syringe is fitted to an ultrasound transducer for applying ultrasound energy to the fluorocarbon (e.g., perfluorocarbon) nanoemulsion.

In certain embodiments of the pre-filled syringe, the ultrasound is characterized by having a frequency ranging from about 10 KHz to about 10 MHz.

In yet another aspect, the invention generally relates to a composition of a fluorocarbon (e.g., perfluorocarbon) nanoemulsion prepared by the method disclosed herein.

In certain embodiments of the composition, the composition is prepared from a fluorocarbon (e.g., perfluorocarbon) nanoemulsion enclosed within a sealed container wherein the particle size of the fluorocarbon (e.g., perfluorocarbon) is greater than about 1 micron.

In certain embodiments of the composition, after exposure to ultrasound the mean particle size is less than 500 nm.

In yet another aspect, the invention generally relates to a method for reducing particle size of a fluorocarbon (e.g., perfluorocarbon) nanoemulsion. The method comprising: providing a fluorocarbon nanoemulsion enclosed within a syringe, and passing the fluorocarbon nanoemulsion through a length of tubing en route to a subject wherein the fluorocarbon nanoemulsion is passed through an ultrasound field resulting in the mean particle size of the fluorocarbon nanoemulsion is decreased by 10% or more.

In certain embodiments of the method, the mean particle size of the fluorocarbon (e.g., perfluorocarbon) nanoemulsion is decreased by 30% or more. In certain embodiments of the method, the mean size of the fluorocarbon (e.g., perfluorocarbon) nanoemulsion is decreased by 50% or more.

In certain embodiments of the method, the mean particle size of the fluorocarbon (e.g., perfluorocarbon) nanoemulsion prior to passing through the ultrasound field is greater than about 1 micron. In certain embodiments of the method, the mean particle size of the fluorocarbon (e.g., perfluorocarbon) nanoemulsion after passing through the ultrasound field is less than 500 nm.

BRIEF DESCRIPTION OF THE DRAWINGS

The invention will be better understood from a reading of the following detailed description taken in conjunction with the drawings in which like reference designators are used to designate like elements, and in which.

DEFINITIONS

Figure 1:
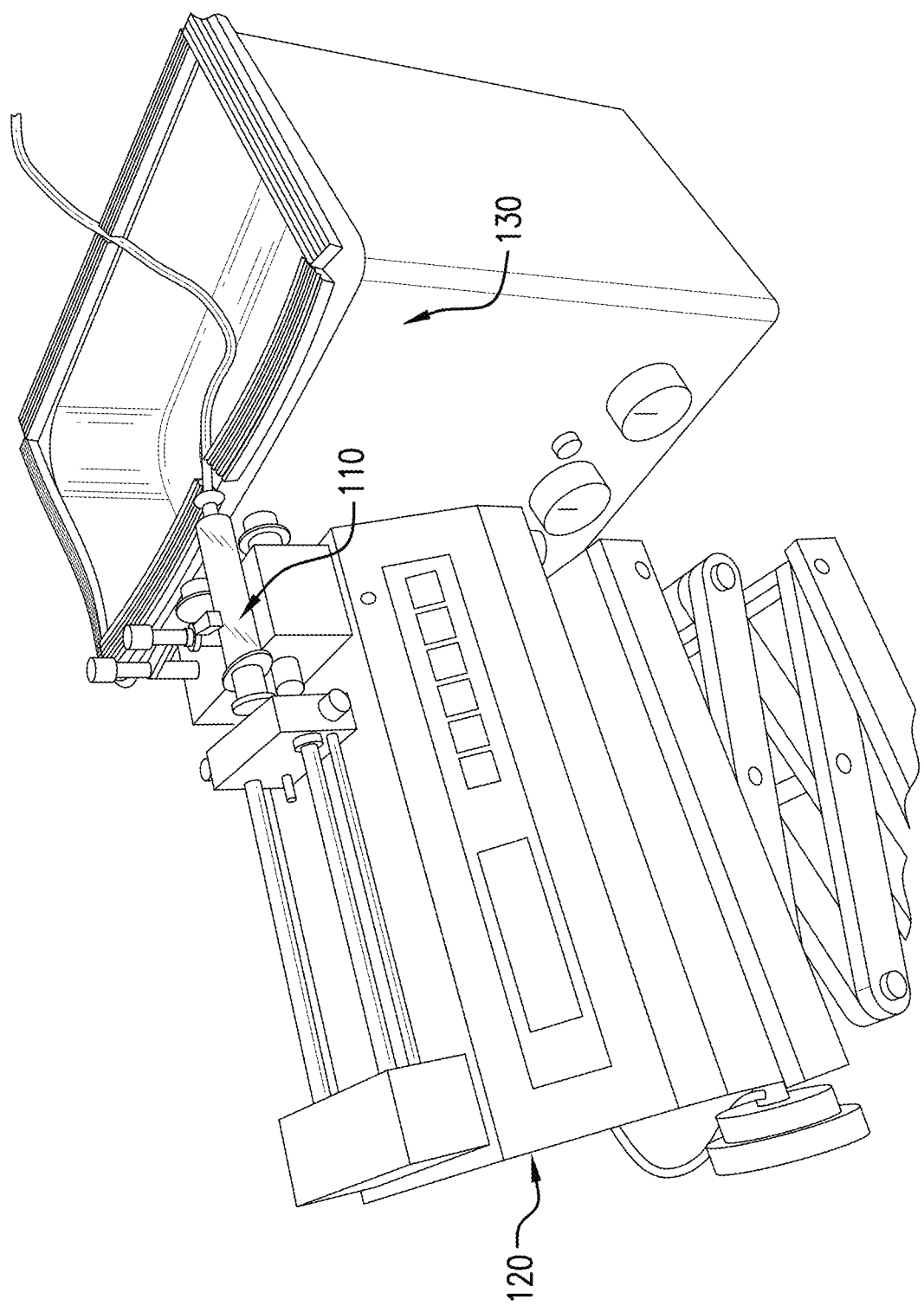
FIG. 1 shows an exemplary embodiment of equipment used for in-line ultrasonication of either an out-of-specification nanoemulsion or a coarse emulsion generated by vortexing of a glass vial of combined components of the nanoemulsion followed by aspiration of the coarse emulsion into a syringe.

Unless defined otherwise, all technical and scientific terms used herein have the same meaning as commonly understood by one of ordinary skill in the art to which this invention belongs.

As used herein, "administration" of a disclosed compound or composition encompasses the delivery to a subject of a pharmaceutical composition using any suitable formulation or route of administration, as discussed herein.

As used herein, the term "mechanical vibration" refers to the application of an oscillatory motion to an object such as a container (e.g., a vial or a syringe) using any device that can impart motion to the object or a device capable of imparting energy of any frequency to a static object wherein the energy is at least partially transmitted to the object such as a content in a container. Sonication, including untrasonication, is a form of mechanical vibration.

For example, a vial may be placed on the oscillating rubber cup of a vortexing apparatus and held there while the vortexing apparatus is in motion. The vortexer imparts a circular or elliptical motion or an approximately circular or elliptical motion to the bottom of the vial via its rubber cup in which the vial is seated which leads to motion of the vial and also agitation of the contents. The energy imparted into the vial and the contents of the vial can be varied depending on the speed of the vortexing motion.

Mechanical vibration may also encompass the process of imparting energy to a vial or syringe or other container and its contents by using an oscillator or a transducer that provides a sonic frequency that, for example, can be an ultrasonic frequency that by appropriate means is transmitted to the vial or a syringe or another type of container. The energy may be transmitted by direct contact of the oscillator or transducer with the vial, syringe or other container which then may transmit the energy at the given or altered frequency and attenuation through the vial wall, syringe surface or container wall to the contents of the vial, syringe or container, respectively. The oscillator or transducer may be placed at or on any part of the vial, syringe or container and may also be placed proximal to any part of the vial, syringe or container but not contacting it so long as a suitable transmission of at least some fraction of the sonic energy is effected the oscillator or transducer and the vial, syringe or container. Examples of frequency transmission include a water bath, a layer of gel or a solid material such as a metal surface, which contacts the oscillator or transducer and the vial, syringe or container.

As used herein, the term "nanoemulsion" refers to a suspension or emulsion of nanodroplets in aqueous media. The term "nanodroplet" refers to submicron droplets comprising a liquid fluorocarbon or perfluorocarbon. It is noted that, as used herein, the term "nanoemulsion" is sometimes used to refer to emulsions with out-of-specification particle sizes that are, unless remedied, not suitable for their intended applications.

As used herein, the term "NVX-108" refers to a dodecafluoropentane (DDFP) nanoemulsion (DDFPe) stabilized by the fluorosurfactant PEG-Telomer B and suspended in sodium phosphate-buffered 30% aqueous sucrose solution.

As used herein the term "fluorocarbon" or "FC" refers to substances wherein the majority of carbon-hydrogen bonds are replaced by carbon-fluorine bonds. In this class of materials the compounds may also have amine, ether, alkene, alkyne, alkane groups as well as aromatic groups and even heteroaromatic groups whose C—H bonds are replaced, but not completely replaced by carbon-fluorine bonds.

As used herein, the term "perfluorocarbon" or "PFC" refers to a substance wherein all carbon-hydrogen bonds are replaced with carbon-fluorine bonds. As in the case of fluorocarbons, the perfluorocarbons may have amino, ether, alkene, alkyne, alkane groups as well as aromatic groups and even heteroaromatic functional groups but in each case all carbon-hydrogen bonds are replaced with carbon-fluorine bonds. It is noted that, unless noted otherwise, where an embodiment refers to a "FC" the disclosed invention also includes a corresponding embodiment with a PFC.

Liquid fluorocarbons and perfluorocarbons may be selected from materials that may have other functions such as amino, ether, alkene, alkyne, alkane, aryl or even heteroaryl groups, any of which may bear another halogen besides fluorine, for example a chorine atom or a bromine atom. Furthermore the C—H bonds are largely (in the case of fluorocarbons) or completely replaced (as in the case of perfluorocarbons) with carbon-fluorine bonds. The carbon containing groups of the amines, ethers, alkenes, alkynes or alkanes may range from 4 carbons to 8 carbons in length.

In the case of perfluoroalkanes, perfluoroalkenes and perfluoroalkynes, the preferred carbon chain length is determined by the boiling point of the substance. Where the boiling point of the 5 carbon chain length material is below 25° C. the 6 carbon chain is preferred, where the boiling point of the 5 carbon chain length material is 25° C. to 30° C. 5 carbon atoms is the preferred chain length. In the case of perfluoroalkanes where all of the carbon-hydrogen bonds are replaced by carbon-fluorine bonds the preferred materials are wherein the chain length is 6 carbon atoms and most preferably 5 carbon atoms. In the case of perfluoroalkanes the preferred perfluorocarbon is dodecafluoropentane which preferably consists of dodecafluoro-n-pentane as the major component but wherein other structural isomers may be present at a level of up to 23%. Even more preferred is dodecafluoro-n-pentane where the presence of other isomers is minimized, ideally to a level of less than 2%.

As used herein, a "pre-filled syringe" refers to a syringe (e.g., glass or plastic syringes) having a syringe barrel, one end of which accepts a plunger that has a fluid and gas tight piston assembly which inserts into the barrel and an exit port which can be fitted with a needle or other suitable assembly. For example, a two way stopcock can be fitted which can be deployed to close off the exit port. At time of administration, such a stopcock assembly, which is affixed to the syringe, can be attached to a needle or suitable connection to apparatus that will allow administration of the syringe contents to a patient.

It is understood that the assembly of components fitted to the exit port may have other functions besides closing or opening the contents of the syringe to another assembly affixed to the syringe. For example, there may be, as part of the assembly a component, such as a transducer, which is capable of transmitting ultrasound energy to the contents of the syringe before or during administration.

As used herein, the term "sonication" refers to a subset of mechanical vibration wherein sonic energy generated using a transducer or a probe or other mechanism capable of generating the desired frequency at the desired power, is transmitted to the contents of a container such as a vial or a prefilled syringe. The frequency of such sonic energy may be from 10 KHz to as much as 10 MHz. In this disclosure, when referring to sonication at frequencies less that 20 KHz it is understood that such frequencies are not technically ultrasound as they are in the audible range. As used herein, the term "ultrasonication" refers to sonication using a frequency or frequencies in the inaudible frequency range above about 20 KHz, generally from about 20 KHz to about 1 MHz. As those skilled in the art will appreciate, ultrasonication comprises the transmission of ultrasound energy.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

DETAILED DESCRIPTION OF THE INVENTION

The invention provides methods and devices that adjust particle size of FC/PFC nanoemulsions, and efficiently and effectively return the product to particle size parameters within specification. Methods and devices of the invention can be employed at the manufacturing site or at the point of use employing widely available equipment. Mechanical vibrations (e.g., sonication and ultrasonication) provide the required energy to allow the desired adjustment (e.g., reduction) in particle size to the values comparable to freshly prepared material via high-pressure homogenization. Novel pre-filled syringes and injection systems are also disclosed that ensure particle size optimization and product safety and efficacy. The methods and devices of the invention allow the use of previously out-of-specification products for the expected applications once rectified, reducing waste of the product at the manufacturing site and/or the marketplace.

The method most commonly employed for preparation of PFC nanoemulsions is high-pressure homogenization. For example, preparation of a DDFP nanoemulsion using high-pressure homogenization is typically carried out as follows.

A cold jacketed, closed vessel Pressure Vessel 0 (PV0) pressurized to about 10 psi with nitrogen, containing a solution of WFI (water for injection) 6% wt/vol in PEG-Telomer B and about 40% wt/vol in DDFP is stirred at 2-6° C. for 1 hour at about 300 to 600 rpm. PV0 is connected via valved sanitary fittings to the inlet and outlet of an Avestin® EmulsiFlex-C50 high pressure homogenizer (Avestin Inc, Ontario Canada) and the material is subjected to continuous homogenization at about 7000 psi for about 20 min. Using appropriate valving and tubing lines the homogenized solution is then transferred, under zero homogenization pressure, from the homogenizer to a ~12-fold volume cold-jacketed pressure vessel (PV1) containing about a 10-fold volume amount of a stirred phosphate-buffered (pH about 7) solution of 30% sucrose in WFI at about 4° C. This solution is stirred for about 15 min. under a pressurized nitrogen atmosphere (~10 psi). Using appropriate valving and tubing lines the solution is transferred from PV1, through the homogenizer at a homogenization pressure of about 7000 psi to a third cold-jacketed pressure vessel (PV2) of the same size as PV1. The material is stirred in PV2 for about 15 min. under a nitrogen pressure of about 10 psi and then transferred via nitrogen pressure through a 0.8/0.2 micron Supor AcroPak™ 500 in-line filter to a fourth cold jacketed pressure vessel (PV3). The resulting material is then stirred for about 15 min. and then sterile vials of appropriate size for the given application are filled and crimp capped in a sterile laminar flow hood using a peristaltic pump calibrated to deliver the desired volume of material. The material is stored at constant temperature in a standard stability chamber.

As is disclosed herein, FC/PFC nanoemulsions tend to exhibit growth in particle size over time. This is undesirable because large particle size, e.g. particles over 2 microns in size, may increase the risk of adverse events, in particular associated with vascular (e.g. IV) administration of the particles.

Extensive studies were carried out in production of perfluorocarbon nanoemulsions by high-pressure homogenization of a primary emulsion of perfluorocarbon and surfactant, dilution of the homogenizate with a continuous phase, which may optionally contain excipients such as sucrose and a buffer, followed by submicron filtration as the sterilization step. Perfluorocarbon emulsions cannot be heat-sterilized due to the volatility of the perfluorocarbon component and possible degradation of one or more excipients. Therefore, aseptic filtration directly before filling is employed to assure sterility of the product.

Table 1 shows exemplary and typical sub-micron particle size data for freshly prepared emulsions of DDFP in combination with Peg Telomer B (PTB), a perfluoroalkyl-ethyl-polyethoxylated—alcohols, surfactant(s), and phosphate buffered aqueous sucrose.

TABLE 1

Particle Size for Batches of Buffered DDFP/Peg-Telomer B/Buffered Sucrose Emulsions Prepared by High-Pressure Homogenization

| Batch No. | IWMD (nm) | Std. Dev. (nm) | VWMD (nm) | NWMD (nm) | SD (%) | IWCUM 99%< (nm) | VWCUM 99%< (nm) | Xi Sq |
|---|---|---|---|---|---|---|---|---|
| 1 | 222.4 | 78 | 195.5 | 116.6 | 35.1 | 471.3 | 426.1 | 0.51 |
| 2 | 222.1 | 78 | 194.5 | 114.3 | 35.1 | 474.2 | 415.1 | 0.36 |
| 3 | 241.3 | 72 | 230.3 | 157.9 | 29.8 | 461.8 | 440.6 | 0.23 |
| 4 | 242.9 | 81 | 227.7 | 140.1 | 33.4 | 498.1 | 466.6 | 0.25 |
| Average | 232.2 | 77 | 212.0 | 132.2 | 33.3 | 476.4 | 437.1 | 0.34 |
| SD | 11.5 | 4 | 19.7 | 20.7 | 2.5 | 15.4 | 22.3 | 0.13 |
| RSD (%) | 4.9 | 5 | 9.3 | 15.7 | 7.4 | 3.2 | 5.1 | 38.05 |

Characteristics of freshly prepared material include: The VWMD (Volume Weighted Mean Diameter) is less that the IWMD (Intensity Weighted Mean Diameter) and the NWMD (Number Weighted Mean Diameter) is less than both the IWMD and VWMD. Values of these parameters for typical batches are shown in Table 1. Chi squared (goodness of fit to a unimodal Gaussian Distribution, also referred to as Xi Sq or $Xi^2$) values usually do not exceed 0.75, but typically are 0.17 to 0.40, indicating that the obtained dynamic light scattering data is consistent with the existence of the particles as a unimodal Gaussian distribution. For the present purposes, an out-of-specification value set for IWMD and IWCUM99%< would be >600 nm and >1300 nm, respectively.

Stability of these emulsions depends on a number of variables, including the components, storage conditions, concentration, and container headspace. Instability of nanoemulsions is typically manifested by particle growth by the mechanism of Ostwald ripening, which over time may result in the emulsion having particles of greater size than the specified range. When such an event occurs, an accompanying complication is that the size limit for which 99% of the particles must not exceed (99% Cumulative Distribution<) is often exceeded beyond the allowable specification for that parameter, rendering the product not suitable for use in the desired application.

Based on extensive studies of FC/PFC (e.g., perfluoropentane, perfluorohexane) nanoemulsions, it was observed that particle growth of sterile nanoemulsions was not usually accompanied by component degradation. Typically, the only undesirable attribute of the nanoemulsions was the high particle size and CUM99%<values.

Methods and devices disclosed herein can return the product to particle size parameters within specification and allow the use of the product for the expected application, thus avoiding its unsafe use and reducing product waste. A significant benefit of the disclosed devices and methods is that the "rectification" process does not involve removing the sterile product from its container, nor does it require heating or cooling the product. The process is accomplished in a short period via a simple procedure. The disclosed methods and devices are particularly suitable for these products, which have volatile perfluorocarbon (or other volatile) components.

By not requiring or involving opening of the container housing the nanoemulsion, the risk of microbial contamination is minimized and the cost associated with maintaining sterilization is avoided.

Methods and devices of the invention can be employed at the manufacturing site or at the point of use employing widely available equipment. Low power ultrasonication, which produces numerous local zones where cavitation occurs, affords the required energy to allow the desired reduction in particle size to the values obtained from preparation of the material via high-pressure homogenization. Furthermore, novel pre-filled syringes and injection systems are disclosed herein that are designed to ensure particle size optimization and product safety and efficacy.

It has been surprisingly discovered that mechanical vibrations (e.g., sonication and in particular ultrasonication) can be effectively and efficiently used to adjust (e.g., decrease) particle sizes in FC/PFC nanoemulsions as the nanoemulsions are disposed within a sealed container.

In certain embodiments, the container wherein the FC/PFC nanoemulsion is situated comprises a glass vial. In certain embodiments, the container comprises a plastic vial. In certain embodiments, the container comprises a pre-filled syringe having the FC/PFC emulsion loaded therein.

In certain embodiments, the FC/PFC nanoemulsion comprises a pre-made emulsion, e.g., prepared by high-pressure homogenization. In certain embodiments, the PFC nanoemulsion comprises a mixture of the PFC, aqueous phase, and one or more excipients, where that mixture has not previously been subjected to homogenization.

In certain embodiments, the vial or syringe is optionally subjected to an agitation step, which can be a manual shaking step or a vortexing step before sonication. In certain embodiments, the PFC nanoemulsion is subjected to sonication in association with a syringe pump or power injector. In certain of these embodiments, the sonication may be applied to the syringe body, the syringe plunger, tubing exiting the syringe, or the tip of the syringe or parts proximal or distal to the tip of the syringe, such that the material is subjected to sonication prior to injection into the patient.

In certain embodiments, the frequency of the sonication energy ranges from about 1 KHz to about 10 MHz. In certain embodiments, the frequency of the sonication energy ranges from about 10 KHz to 20 KHz. In certain embodiments the frequency of the sonic energy comprises 10 KHz to about 10 MHz.

In certain embodiments, the frequency of the sonication energy ranges from about 10 KHz to about 20 KHz. In certain embodiments, the frequency of the sonication energy ranges from about 20 KHz to about 5 MHz. In certain embodiments, the frequency of the sonication energy ranges from about 5 MHz to about 10 MHz. In certain embodiments, the frequency of the sonication energy ranges from about 40 KHz to about 1 MHz. In certain embodiments, the frequency of the sonication energy ranges from about 40 KHz to about 100 KHz. In certain embodiments, the frequency of the sonication energy ranges from about 100 KHz to about 500 KHz. In certain embodiments, the frequency of the sonication energy ranges from about 500 KHz to about 1 MHz.

In certain embodiments, the sonication energy is swept in frequency, e.g., from about 5 KHz (sonication), 10 KHz (sonication), 20 KHz, 30 KHz, 40 KHz or 50 KHz, to about 100 KHZ, 500 KHz, 1 MHz, 2 MHz, 5 MHz or 10 MHz (all frequencies 20 KHz to 10 MHz can be considered ultrasonication). In certain embodiments the sonication energy is swept in frequency over a range of +/−1 percent to about +/−10 percent of the nominal frequency of the ultrasound applied. By way of an example, if the nominal ultrasound frequency is 40 KHz the frequency may be swept through a range of 39.6 KHz to 40.4 KHz or as much as 36 KHz to 44 KHz. For succeeding sweep ranges discussed below the calculation is done in the same manner.

In certain embodiments the sonication or ultrasonication energy is swept in frequency over a range of +/−1 percent to about +/−20 percent of the nominal frequency of the ultrasound applied. In certain embodiments the sonication energy is swept in frequency over a range of +/−1 percent to about +/−50 percent of the nominal frequency of the ultrasound applied. In certain embodiments the sonication energy is swept in frequency over a range of +/−1 percent to about +/−70 percent of the nominal frequency of the ultrasound applied. In certain embodiments the sonication or ultrasonication energy is swept in frequency over a range of +/−1 percent to +/−100 percent of the nominal frequency applied. Frequency sweeps smaller or larger than the specified examples are contemplated herein.

In certain embodiments the delivered ultrasound energy is not limited to the energy transmitted at the nominal sonication or ultrasonication frequency. The ultrasound energy includes that transmitted at the nominal ultrasound frequency and its associated harmonics. For example, with ceramic-stacked piezoelectric transducers the third and higher harmonics contribute more sonication energy than contributed at the nominal transducer energy.

In certain embodiments, the power of the sonication or ultrasonication energy ranges from about 0.1 Watt to about 200 Watts (e.g., from about 0.1 Watt to about 5 Watts, from about 0.1 Watt to about 10 Watts, from about 0.1 Watt to about 20 Watts, from about 0.1 Watt to about 50 Watts, from about 0.1 Watt to about 100 Watts, from about 0.5 Watt to about 200 Watts, from about 1.0 Watt to about 200 Watts, from about 10 Watts to about 200 Watts, from about 20 Watts to about 200 Watts, from about 50 Watts to about 200 Watts, from about 100 Watts to about 200 Watts, from about 2 Watts to about 20 Watts).

In certain embodiments, the sonication or ultrasonication energy is applied to the PFC nanoemulsion for a time duration of from about 1 second to about 30 min. (e.g., from about 1 sec. to about 25 min., from about 1 sec. to about 20 min., from about 1 sec. to about 15 min., from about 1 sec. to about 10 min., from about 1 sec. to about 5 min., from about 1 sec. to about 1 min., from about 1 sec. to about 2 min, from about 1 sec. to about 3 min, from about 10 sec. to about 30 min., from about 30 sec. to about 30 min., from about 1 min. to about 30 min., from about 5 min. to about 30 min., from about 10 min. to about 30 min., from about 1 min. to about 5 min., from about 5 min. to about 15 min., from about 15 min. to about 25 min.). In certain embodiments, the sonication or ultrasonication energy is applied for time durations less than about 60 seconds.

In certain embodiments, the sonication or ultrasonication energy is applied intermittently. This type of treatment is variation of the duty cycle for the transducer. For example the transducer may be powered for 5 seconds followed by a period of 5 seconds wherein the transducer is not powered and this carried out for a prescribed total period of time, for example 4 min.; in this case the duty cycle for the transducer is a 50% duty cycle. Duty cycles of 1% up to 100% can be employed in any embodiment described herein where sonication or ultrasonication is employed for preparing fluorocarbon or perfluorocarbon nanoemulsions of the desired particle size, whether from a preexisting nanoemulsion or from a coarse emulsion prepared by agitation of premixed components in a vial or in a syringe assembly, which includes any components of such an assembly wherein the coarse emulsion or the preexisting nanoemulsion can be accessible to the irradiation.

In certain embodiments, the sonication energy is applied directly to the wall of the vial or syringe with a piezoelectric transducer. In certain embodiments, the sonication energy is applied directly to the wall of the vial or syringe with a ceramic transducer or other transducer.

In certain embodiments, the vial or syringe tubing (e.g., exiting the syringe) may be placed within a water bath for application of sonic energy.

In certain embodiments, the sonication energy is applied to the syringe and its contents via a permanently placed or removable ultrasound transducer situated within the plunger of the syringe.

In certain embodiments the sonication or ultrasonication is applied to the syringe via a transducer placed at the end of the syringe between the end of the syringe and the beginning of the assembly that begins the path of the syringe contents immediately post exit of the syringe.

In certain embodiments the sonication or ultrasonication is applied to the syringe via a transducer placed at the end of the syringe wherein the transducer is in contact either directly or via a coupling medium with a small coiled section of tubing which is irradiated by the transducer as the syringe contents pass through it directly before delivery to the subject or the patient.

The transducer may be concentric with the interior of the plunger or asymmetrically placed with respect to the X, Y or Z-axis of the plunger.

The transducer dimensions may span any proportion of the length, width or depth of the allowed space within the syringe plunger.

In an exemplary embodiment, a disposable syringe whose plunger has a cylindrical interior space into which fits a reusable transducer is used. The syringe, containing the components of the nanoemulsion which have been agitated by shaking, vortexing or other means to suspend the components, is loaded into a power injector or a syringe pump and the reusable transducer is fitted into the interior of the plunger. Alternately, the transducer may be fitted into the plunger followed by loading of the assembly into the power injector or syringe pump. The transducer may be powered for a prescribed period before injection is initiated and then power to the transducer stopped prior to injection. Alternately, after the pre-injection powering of the transducer, the injection can be initiated with continuous application of power to the transducer or intermittent application of power to the transducer at an optimized duty cycle that may range from 1% to 100%.

In certain embodiments, the transducer may be a ring transducer or a conical ring transducer placed respectively on the body of the syringe at or near the juncture of the point at which the products exits the syringe end during injection respectively. The outer surface of the transducer may be constructed to physically mate to the contours of the section of the syringe it is fitted to, which will be determined by the type of syringe employed. The transducer can be actuated before injection for a specified period from as low as 1 second to as much as 30 min. (e.g., for about 5 sec. 10 sec. 30 sec., 1 min., 3 min., 5 min., 10 min., 15 min. 20 min., 25 min.) before injection of the product is initiated.

In certain embodiments, the sonication energy is applied using non-contact ultrasound transducers. In such embodiments, the transducer frequency can be from 30 KHz to 5 MHz, for example. The non-contact transducers transmit the required ultrasound through air, requiring no contact surface or coupling fluid between the transducer and the vial, syringe, syringe components, tubing, or needle employed in the apparatus employed to prepare and deliver the PFC nanoemulsion. Examples of such non-contact transducers include those available from The Ultran Group (3100 Research Drive, State College, Pa. 16801 USA). Such non-contact transducers can be provided in circular, square, point focus, and cylindrical focus configurations.

In certain embodiments, the ultrasound power source may be varied to suit a particular application. In certain embodiments, the ultrasound frequency is selected such that the wavelength of the ultrasound power matches the diameter, or a specific fraction of the tubing or the syringe or vial. For example, if the frequency of a water bath sonicator ranges from 10 to 30 KHz, the wavelength of that ultrasound energy is approximately 160 mm to about 50 mm, which is generally larger than the diameter of the vials, syringes, and the tubing exiting from a syringe.

In certain embodiments, using transducers and appropriate software, ultrasound may be focused in a specific region of a syringe, a syringe component, or tubing leading into or out of a syringe. By defining this space and adjusting the distance from the transducer to the space to be sonicated, one can employ focused ultrasound to sonicate the previously agitated mixture of components in an in-line system that allows modification of the previously agitated mixture of components to provide the perfluorocarbon emulsion having the desired particle size specifications. In certain embodiments, the application of the focused ultrasonication is continuous. In certain embodiments, the application of the focused ultrasonication is intermittent at an optimized duty cycle which may range from 1% to 100%.

Ultrasound of about 500 KHz to about 10 MHz has a wavelength of about 3 millimeters to about 0.16 millimeters and can be applied, for example, to tubing exiting a syringe. By controlling the infusion rate with a pump, which is integrated into a system that incorporates power delivery with flow rate, the size of the particles can be controlled. By selecting the ultrasound frequency to suit the particular component of the system (syringe body, syringe body exit, tubing that carries the material from the syringe to the injection site) as opposed to using only one frequency of ultrasound regardless of the system component being sonicated, one can ensure that the ultrasound energy is appropriate for the particular application, namely sonication of the vial, syringe, and/or tubing.

It has been found that that changing the frequency of the ultrasound energy does not focus the ultrasound. Rather, changing frequency determines how many periods of the energy sine wave exist in the space that is being sonicated. A long wavelength sonication of a small space effectively presents a small section of the sine wave to the small space, so the energy at different points in the small space is similar and there is not variation of energy level with time. Using a short wavelength presents the sample with multiple sine waves of period smaller than that of the sample space.

In certain embodiments, the ultrasound may be focused to localize the energy to a very small area within a larger space. All of the energy is deposited in that space with the same amplitude. As an analogy, think of a lens that gathers all light from the entrance side and concentrates it to a point somewhere past the exit side.

In certain embodiments, the sonication of the previously agitated mixture of components can be performed during aspiration into the syringe. As the aspirated material passes the appropriately located transducer the sonication of the material is conducted during the aspiration, before injection, to give the FC/PFC nanoemulsion the desired particle size distribution within the syringe.

Where sonication during aspiration is employed, the transducer may be located at tubing attached to the inlet of the syringe, at the inlet portion of the syringe, in the body of the syringe proximal to the inlet of the syringe, within the plunger of the syringe or on any portion of the syringe barrel. Depending on the location of the transducer, the optimization of the sonication power level and/or frequency and duty cycle can be conducted to provide the most efficient production of the perfluorocarbon emulsion having the required particle size distribution. After aspiration of all of the needed material into the syringe sonication may be optionally continued or stopped and injection of the perfluorocarbon emulsion imitated.

The optional agitation step may be conducted according to the application. For example, manual shaking can be performed for a period from 15 seconds to as long as 3 min. (e.g., for about 30 sec., 1 min., 2 min.). For example, vortexing may be performed at a range of different rpm's ranging from about 1,000 rpm to about 5,000 rpm (e.g., about 1,000 rpm, 2,000 rpm, 3,000 rpm, 4,000 rpm, 5000 rpm). The cycle stroke on the vortexer may vary from about 1 mm to about 10 mm (e.g., about 3 mm, 5 mm, 7 mm, 9 mm). The vortexing step may last from about 1 second to about 5 min. (e.g., for a time duration of about 10 to 60 sec., 30 sec. to 2 min., 1 min. to 3 min.). The vortexing may be applied in the form of mechanical vibration to a sealed vial or pre-filled syringe. The amplitude of each vibration may result in an excursion of from about 1 mm to about 10 mm (e.g., about 3 mm, 5 mm, 7 mm, 9 mm).

The FC or PFC may comprise a linear or branched fluorocarbon material ranging in carbon length from about 1 carbon to about 10 carbon atoms. Useful FC/PFC include perfluorobutane, perfluoropentane, perfluorohexane, perfluoroheptane, perfluorooctane, perfluorononane, perfluorodecalin, perfluorooctylbromide, perfluorotripropylamine and perfluorotributylamine. Preferred PFCs include perfluoropentane, perfluorohexane, perfluoroheptane and perfluorooctane. Most preferred is perfluoropentane. The concentration of the FC/PFC in the final emulsion may vary from about 0.1% by weight to about 100% by weight. More preferably the concentration is from about 1% by weight to about 50% by weight/volume. Still more preferably the concentration is from about 2% w/vol to about 10% w/vol.

The FC/PFC is emulsified via one or more surfactants that are included within the container. Useful surfactants include but are not limited to PEG-Telomer-B, DuPont Capstone FS-3100 and related Capstone brand fluorosurfactants and phospholipids and mixtures thereof. A particularly useful phospholipid mixture comprises DPPC, DPPE-MPEG (5,000) and DPPE. Components of phospholipid formulations for preparation of fluorocarbon or perfluorocarbon nanoemulsions may also include DPPE-MPEG or DSPE-MPEG compounds wherein there are little as 1 to as many as 113 oxyethylene units as well as mixtures of such compounds. Similarly the DPPC may be replaced with DSPC and DPPE pay be replaced with DSPE. Such replacements of one or more components may be employed to optimize the performance of the perfluorocarbon nanoemulsions.

Preferably the surfactant concentration varies from about 0.1 mg/mL to about 100 mg/mL. As one skilled in the art would recognize the concentration of surfactant will vary depending upon the concentration of the FC. As an example, using 2% w/vol DDFP, the surfactant concentration employed can be about 0.3% by weight/volume. Where desired the ratio of surfactant to DDFP and their absolute percentages can be varied to optimize the particle size and/or total dose or container size for a particular application. For example a nanoemulsion of DDFP can be prepared using 4% DDFP weight/volume and 0.3% PTB weight volume to provide a more concentrated nanoemulsion.

The aqueous phase of the emulsion may comprise water (e.g. WFI), saline, PBS or aqueous media with other buffer(s). In addition, other excipients such as sucrose, propylene glycol, glycerol, polyethylene glycol singly or in combination or other materials may be added into the containers comprising the FC/FC emulsion.

In one aspect, the invention generally relates to a method for reducing particle size of a perfluorocarbon nanoemulsion. The method includes applying mechanical vibration to the perfluorocarbon emulsion for a time duration sufficient to adjust the particle size of the perfluorocarbon emulsion to a pre-selected value. The perfluorocarbon nanoemulsion comprises a perfluorocarbon having from 4 to about 10 carbon atoms in length.

In certain embodiments, the perfluorocarbon emulsion is enclosed in a vial or pre-filled syringe.

In certain embodiments, the mechanical vibration comprises ultrasound. In certain embodiments, the ultrasound is characterized by a frequency from about 10 KHz to about 10 MHz. In certain embodiments, the perfluorocarbon is from about 4 to about 8 carbon atoms in length.

In certain embodiments of the method, the fluorocarbon is a perfluorocarbon. In certain embodiments, the perfluorocarbon comprises perfluoropentane, perfluorohexane, or both.

In certain embodiments of the method, the perfluorocarbon consists of perfluoropentane.

In certain embodiments of the method, the perfluorocarbon consists of perfluorohexane.

In another aspect, the invention generally relates to a pre-filled syringe of a fluorocarbon (e.g., perfluorocarbon) nanoemulsion, wherein the fluorocarbon is from about 4 to about 10 carbon atoms in length and the fluorocarbon nanoemulsion is from about 0.1% to 50% weight volume of the fluorocarbon.

In certain embodiments of the pre-filled syringe, wherein the fluorocarbon is a perfluorocarbon. In certain embodiments, the perfluorocarbon is from about 4 to about 8 carbon atoms in length.

In certain embodiments of the pre-filled syringe, the fluorocarbon is a perfluorocarbon. In certain embodiments, the perfluorocarbon comprises perfluoropentane, perfluorohexane, or both.

In certain embodiments of the pre-filled syringe, the perfluorocarbon consists of perfluoropentane.

In certain embodiments of the pre-filled syringe, the perfluorocarbon consists of perfluorohexane.

In certain embodiments of the pre-filled syringe, the syringe is made from a material comprising glass, plastic, or both.

In certain embodiments of the pre-filled syringe, the syringe is made from a glass material.

In certain embodiments of the pre-filled syringe, the syringe is made from a plastic material.

In certain embodiments of the pre-filled syringe, the syringe is fitted to an ultrasound transducer for applying ultrasound energy to the fluorocarbon (e.g., perfluorocarbon) nanoemulsion.

In certain embodiments of the pre-filled syringe, the ultrasound is characterized by having a frequency ranging from about 10 KHz to about 10 MHz.

In yet another aspect, the invention generally relates to a composition of a fluorocarbon (e.g., perfluorocarbon) nanoemulsion prepared by the method disclosed herein.

In certain embodiments of the composition, the composition is prepared from a fluorocarbon (e.g., perfluorocarbon) nanoemulsion enclosed within a sealed container wherein the particle size of the fluorocarbon (e.g., perfluorocarbon) is greater than about 1 micron.

In certain embodiments of the composition, after exposure to ultrasound the mean particle size is less than 500 nm.

In yet another aspect, the invention generally relates to a method for reducing particle size of a fluorocarbon (e.g., perfluorocarbon) nanoemulsion. The method comprising: providing a fluorocarbon nanoemulsion enclosed within a syringe, and passing the fluorocarbon nanoemulsion through a tubing en route to a subject wherein the fluorocarbon nanoemulsion is passed through an ultrasound field resulting in the mean size of the fluorocarbon nanoemulsion is decreased by 10% or more.

In certain embodiments of the method, the mean size of the fluorocarbon (e.g., perfluorocarbon) nanoemulsion is decreases by 30% or more. In certain embodiments of the method, the mean size of the fluorocarbon (e.g., perfluorocarbon) nanoemulsion is decreases by 50% or more.

In certain embodiments of the method, the mean particle size of the fluorocarbon (e.g., perfluorocarbon) nanoemulsion prior to passing through the ultrasound field is greater than about 1 micron. In certain embodiments of the method, the mean particle size of the fluorocarbon (e.g., perfluorocarbon) nanoemulsion after passing through the ultrasound field is less than 500 nm.

In certain embodiments, the perfluorocarbon nanoemulsion disclosed herein comprises one or more phospholipids.

The phospholipids have any suitable carbon chain length, for example, ranging from about 12 carbons to about 18 carbons (e.g., 12, 13, 14, 15, 16, 17, 18) in length.

The phospholipids may account for any suitable weight percentage in the nanoemulsion, for example, from about 0.10% to about 7.5% (e.g., from about 0.10% to about 5%, from about 0.10% to about 4%, from about 0.10% to about 3%, from about 0.10% to about 1.5%).

The disclosure of PCT/US15/35681, titled "Phospholipid Composition And Microbubbles and Emulsions Formed Using Same" and filed Jun. 12, 2015, is expressly incorporated herein by reference for all purposes.

In certain embodiments where the composition comprises a mixture of three phospholipids, exemplary phospholipids and relative amounts there of may be, for example, from about 75 to about 87 mole % phosphatidylcholine, about 5 to about 15 mole % phosphatidylethanolamine and about 3 to about 20 mole % phosphatidylethanolamine-MPEG, wherein "MPEG" refers to a PEG group having a terminus methoxy group. The MPEG herein may have a molecular weight from about 350 to about 5,000 (e.g., from about 350 to about 4,000, from about 350 to about 3,000, from about 350 to about 2,000, from about 500 to about 5,000, from about 1,000 to about 5,000, from about 1,500 to about 5,000, from about 2,000 to about 5,000, from about 3,000 to about 5,000, from about 4,000 to about 5,000). Phosphatidylethanolamine-PEG, where the oligoethyleneoxy portion of the molecule is terminated with a hydroxyl group as opposed to the methoxy terminus present in MPEG phospholipids can be substituted for the phosphatidylethanolamine-MPEG in the formulation. Combinations of phosphatidylethanolamine-MPEG and phosphatidylethanolamine-PEG may also be employed in any relative ratio, as the oligoethyleneoxy-bearing phospholipid component of these formulations.

In embodiments where the composition comprises a mixture of three phospholipids, exemplary phospholipids and relative amounts there of may be, for example, from about 80 to about 85 mole % phosphatidylcholine, about 8 to about 13 mole % phosphatidylethanolamine and about 6 to about 11 mole % phosphatidylethanolamine-MPEG (or phosphatidylethanolamine-PEG).

In certain embodiments, the phosphatidylethanolamine includes a PEG group with a molecular weight from about 350 to about 5,000 (e.g., from about 350 to about 4,000, from about 350 to about 3,000, from about 350 to about 2,000, from about 500 to about 5,000, from about 1,000 to about 5,000, from about 1,500 to about 5,000, from about 2,000 to about 5,000, from about 3,000 to about 5,000, from about 4,000 to about 5,000).

In certain embodiments, compositions of the invention include PEG Telomer B (PTB) a custom purified medical grade of DuPont Zonyl FS-100 or DuPont FSO. In certain embodiments, compositions of the invention include perfluoro-n-hexyl-oligoethyleneoxy-alcohol. A particular form of perfluoro-n-hexyloligoethyleneoxy-alcohol is a fluorosurfactant product known as DuPont Capstone FS-3100 and, in certain embodiments, compositions of the invention include comprises that material or a custom refined version of that material. In certain embodiments, compositions of the invention include tetradecafluoro-n-hexane (TDFH). In certain embodiments, compositions of the invention include tetradecafluorohexane that may consist of a mixture of 2 or more of its possible structural isomers present in any proportions. In certain embodiments, compositions of the invention include dodecafluoro-n-pentane (DDFP). In certain embodiments, compositions of the invention include dodecafluoropentane that may consist of a mixture of 2 or more of its possible structural isomers present in any proportions.

In certain embodiments, compositions of the invention include one or more of dodecafluoro-n-pentane, 1,2-dipalmitoyl-sn-glycero-3-phosphatidylcholine, 1,2-palmitoyl-sn-glycero-3-phosphoethanolamine-N-[methoxy(polyethylene glycol)-5000] salts such as the sodium salt, and 1,2-dipalmitoyl-sn-glycero-3-phosphoethanolamine.

In certain embodiments, compositions of the invention include one or more of 1,2-dimyristoyl-sn-glycero-3-phosphatidylcholine, 1,2-dimyristoyl-sn-glycero-3-phosphoethanolamine-N-[methoxy(polyethylene glycol)-2000] salts such as the sodium salt, and 1,2-dimyristoyl-sn-glycero-3-phosphoethanolamine. In certain embodiments, compositions of the invention include one or more of 1,2-didodecanoyl-sn-glycero-3-phosphatidylcholine, 1,2-didodecanoyl-sn-glycero-3-phosphoethanolamine-N-[methoxy(polyethylene glycol)-2000] sodium salt, and 1,2-didodecanoyl-sn-glycero-3-phosphoethanolamine.

The following examples are presented to further illustrate to persons skilled in the art how to make and use the invention. These examples are not intended as a limitation, however, upon the scope of the invention.

EXAMPLES

Example 1—Reduction of Particle Size by Ultrasonication of a Single Glass. Vial of Aged Nanoemulsion of Dodecafluoropentane—Peg Telomer B—Three Trials In a preliminary study, three samples of an aged emulsion of dodecafluoropentane/Peg Telomer B in buffered 30% sucrose were studied. The original preparation was conducted using high-pressure homogenization and filtration. Particle size data for two of the aged samples was obtained using a PSS Nicomp 380 DLS sub-micron particle sizing apparatus. Intensity-weighted mean diameter (IWMD), volume-weighted mean diameter (VWMD) and number-weighted mean diameter (NWMD) were obtained using the instrument's unimodal Gaussian distribution fitting routine. The Chi-squared values for aged samples were typically 0.75-2.0, which is the upper part of the acceptable range to allow processing of the correlation data assuming a unimodal Gaussian distribution. The standard deviation and cumulative 99%<values were also obtained. The data are shown in Table 2.

output 75 watts). The sample vial was suspended from a support via a 20 gauge copper wire and the vial was immersed up to the neck in the center of the bath. Sonication was performed for the time indicated in Table 1. Sonication of the aged materials gave IWMD, VWMD and NWMD typical or lower than that obtained for freshly prepared material (homogenization method). The effect on reduction of standard deviation of the distribution was not as pronounced but the values trended lower when compared with aged material, approaching the range for freshly prepared material. Sonication dramatically reduced the Cum 99%<value for intensity and volume weighted mean particle diameter. Increasing sonication time from 2 to 10 min. or to a 10 min. sonication followed by a 10 minute waiting period followed by a 15 minute sonication time gave results suggesting that increased sonication time incrementally reduces the mean diameter, standard deviation and CUM 99%<values of the Gaussian for all three categories of particle size.

TABLE 2

Sonication of Aged Samples of DDFP-PTB Emulsion. Effects of sonication time on particle size

| Pre-Sonication | IWMD | IWSD | IWSD % | IWCUM-99% | VWMD | VWSD | VWCUM-99% | NWMD | NWSD | Xi Sq |
|---|---|---|---|---|---|---|---|---|---|---|
| Sample 1 | 583.50 | 361.80 | 62.00 | 2,034.90 | 809.20 | 501.70 | 2,808.10 | 393.60 | 197.60 | 1.88 |
| Sample 2 | 826.10 | 285.00 | 34.50 | 1,735.90 | 930.80 | 321.10 | 1,955.90 | 651.30 | 224.70 | 0.84 |
| Sample 3 | NM | NM | NM | NM | NM | NM | NM | NM | NM | NM |

| Post Sonication Sample # - Sonication protocol | IWMD | IWSD | IWSD % | IWCUM-99% | VWMD | VWSD | VWCUM-99% | NWMD | NWSD | Chi sq |
|---|---|---|---|---|---|---|---|---|---|---|
| Sample 1 - Sonicate 2 min | 219.60 | 80.60 | 36.70 | 481.80 | 188.30 | 69.10 | 413.10 | 105.90 | 38.90 | 0.26 |
| % Change from initial value | -62.37 | -77.72 | -40.81 | -76.32 | -76.73 | -86.23 | -85.29 | -73.09 | -80.31 | -86.17 |
| Sample 2 - Sonicate 10 min | 186.10 | 66.60 | 35.80 | 401.30 | 147.80 | 52.90 | 318.50 | 90.60 | 32.40 | 0.21 |
| % Change from initial value | -77.47 | -76.63 | -3.77 | -76.88 | -84.12 | -83.53 | -83.72 | -86.09 | -85.58 | -75.00 |
| Sample 3 - Sonicate 10 min, wait 10 min, Sonicate 15 min | 183.50 | 50.50 | 27.50 | 334.70 | 160.50 | 44.10 | 292.80 | 122.50 | 33.70 | 0.15 |

The Chi-squared values for the aged samples were significantly elevated when compared with those obtained for freshly prepared (homogenization method) material (Chi-squared typically 0.18-0.35). The mean particle diameter values prior to sonication (see Table 1) were much higher than the values for freshly prepared material (see Table 1). The standard deviation of the distributions generally trended higher as well, namely 34-50% for aged material when compared with 25-35% for freshly prepared material.

Sonication of the aged material was performed using a VWR Aquasonic 75HT ultrasonic cleaning bath (power

Example 2. Reduction of Particle Size of an Aged Nanoemulsion of Dodecafluoropentane-Peg Telomer B by Simultaneous Ultrasonication of Multiple Vials Another trial was conducted wherein 6 vials of aged material were simultaneously sonicated in the ultrasonic cleaning bath to determine if tranches of the aged material can be rectified hence increasing throughput and efficiency.

To establish a baseline for aged material and to determine the variability of particle size parameters, submicron particle sizing of three randomly selected aged samples was conducted. The data are shown in Table 3.

TABLE 3

Particle Size Parameters for Three Aged Samples of DDFP-PTB Nanoemulsion

| Test Article | IWMD (nm) | Std. Dev. (nm) | Std. Dev. (%) | 99% of Dist < (nm) | Xi Sq |
|---|---|---|---|---|---|
| Z | 727.9 | 382.2 | 52.51 | 2149.8 | 1.68 |
| M | 756.6 | 379.8 | 50.20 | 2143.3 | 0.58 |
| A | 683.6 | 375.3 | 54.90 | 2107.4 | 1.57 |
| Average Value | 722.70 | 379.10 | 52.54 | 2133.50 | 1.28 |
| Standard Deviation of Value | 36.78 | 3.50 | 2.35 | 22.84 | 0.61 |
| RSD of Value (%) | 5.09 | 0.92 | 4.48 | 1.07 | 47.45 |

The particle sizing data for the three aged samples showed that the aged samples were quite similar in character as shown by the low RSD indicating that the aging process was relatively uniform across the sample space. The IWMD exceeded the specification of 600 nm and the Cum99%<values significantly exceed the 1300 nm limit. Chi-squared for these samples trended substantially higher than for freshly made material suggesting that the particle size distribution was less well described for the aged material when compared with freshly prepared material.

To evaluate sonication of a tranche of vials of aged material, a set of 6 vials was sonicated simultaneously for 25 min. in a temperature range of 23–25° C. in the ultrasonic cleaning bath. The vials were suspended in 2 rows of 3 vials via 20-gauge stainless steel wire and immersed up to the vial neck. The two rows of vials spanned the central 50% of the length and width of the bath. Particle sizing data for the sonicated samples is shown in Table 4.

TABLE 4

Particle Size Parameters for Six Aged Samples of DDFP-PTB Nanoemulsion Post 25 minutes of Ultrasonication

| Test Article | IWMD (nm) | Std. Dev. (nm) | Std. Dev. (%) | 99% of Dist < (nm) | Xi Sq |
|---|---|---|---|---|---|
| Q | 199.5 | 79 | 39.60 | 463.2 | 0.34 |
| T | 180.6 | 59.6 | 33.00 | 368.4 | 0.45 |
| W | 177.6 | 62.7 | 35.30 | 379.2 | 0.17 |
| S | 173 | 60.6 | 35.03 | 367.2 | 0.27 |
| U | 173.1 | 61.1 | 35.30 | 369.6 | 0.27 |
| V | 176.4 | 66.3 | 37.59 | 394 | 0.17 |
| Average Value | 180.03 | 64.88 | 35.97 | 390.27 | 0.28 |
| Standard Deviation of Value | 9.96 | 7.30 | 2.30 | 37.13 | 0.11 |
| RSD of Value (%) | 5.53 | 11.25 | 6.39 | 9.51 | 38.32 |

Particle size data for all of the ultrasonicated samples were lower than those of freshly prepared material obtained by homogenization (see Table 1 for values of particle size parameters for material freshly prepared using high pressure homogenization). Table 5 compares the average data for aged (3 vials) and simultaneously ultrasonicated aged (6 vials) material.

TABLE 5

Effect of 25 minutes of Sonication of a 6 Vial Tranche of Aged Samples of DDFP-PTB Emulsion on Average Values for IWMD, % Standard Deviation, Cum99% of Distribution < and Xi Sq

| | IWMD (nm) | % Std. Dev. | 99% of Dist < (nm) | Xi Sq$^2$ |
|---|---|---|---|---|
| Pre-Sonication (3 vials) | 722.70 | 52.54 | 2133.50 | 1.28 |
| Post-Sonication (6 vials) | 180.03 | 35.97 | 390.27 | 0.28 |
| % Change in Value | −75.09 | −31.54 | −81.71 | −78.20 |

Dramatic reduction in the IWMD, % standard deviation, Cum99% of Distribution< and Chi-squared values were obtained. The data demonstrates that sonication of an aged material in tranches of vials can efficiently produce a material with the desired IWMD, with narrower particle distribution than the aged material and whose Cum99% of Distribution<values are even lower than that of material freshly prepared using high pressure homogenization. Furthermore the dramatic reduction in the Chi-squared value suggests that the sonicated material particle size distribution is much closer to a true Gaussian distribution than that of the input aged material.

Example 3. Preparation of Dodecafluoropentane—Peg Telomer B Nanoemulsion in Glass Vials by Vortexing the Combined Emulsion Components Followed by Ultrasonication of the Vials—Replacement of High Pressure Homogenization with Ultrasonication as a Means to Prepare High Quality Nanoemulsion in an on Demand Scenario Experiments were performed to see if sonication of sealed vials containing combination of emulsion components at their final concentrations could be used to avoid high-pressure homogenization altogether. The sealed vials were subjected to vortexing followed by ultrasonication resulting in emulsions equivalent to those prepared by high-pressure homogenization.

Each of 4 mL nominal 5 mL capacity (actual capacity 9 mL) vials was charged with 0.44 mL of a solution of PTB in water for injection (WFI, 6% w/v PTB) and 7.44 mL of sucrose in WFI (30% w/v). The vial was capped with a vial stopper, agitated to allow mixture of the ingredients and place in an ice-water bath for 10 min. Then the vial was removed from the ice-water bath, towel-dried and placed on the pan of an analytical balance, and the balance tared to zero weight. A 20 mL screw-capped vial containing DDFP was removed from the freezer (−20° C.) and placed in an ice-water bath. Immediately thereafter, a 1 mL disposable syringe fitted with a ¾" 22 gauge needle was employed to repeatedly aspirate and dispense the cold DDFP in order to cool the syringe. Then a 0.4 mL aliquot of DDFP was aspirated into the syringe and DDFP was delivered into the tared vial until the weight of 0.21 g (2.26% w/v) was dispensed. The vial was immediately stoppered and crimp-capped. Each vial was, in turn, vortexed 1 min. upright, 1 min. inverted and 1 min. upright on a VWR Minivortexer set at the maximum speed. The vial suspended up to its neck, centered left right and front-rear via 20 gauge stainless steel wire in the bath of a VWR Aquasonic 75HT ultrasonic cleaning bath and was ultrasonicated for a prescribed period after which it was allowed to stand for 10 min. before measuring the particle size of the resulting emulsion. The data obtained is given in Table 6.

TABLE 6

Vortexing and Ultrasonication of Combined Components Provides High Quality DDFP-Peg Telomer B Nanoemulsions on Demand

| | Sonication time (min) | IWMD | VWMD | NWMD | SD (%) | IWCUM 99%< | VWCUM 99%< | Xi Sq |
|---|---|---|---|---|---|---|---|---|
| TA002 | 2 | 202.3 | 170.4 | 106.0 | 34.5 | 425.1 | 358.1 | 0.20 |
| TA001 | 2.5 | 219.9 | 189.4 | 107.8 | 36.4 | 479.8 | 413.2 | 0.19 |
| TA003 | 3 | 212.6 | 186.4 | 119.9 | 32.9 | 432.8 | 379.4 | 0.46 |
| TA004 | 3.5 | 192.7 | 157.1 | 98.0 | 35.0 | 408.9 | 333.5 | 0.37 |

Experiments showed that ultrasonication, for even a short period, provides emulsions with particle size parameters indistinguishable from those exhibited by materials prepared using high-pressure homogenization. This demonstrates that ultrasonication can replace high-pressure homogenization for the efficient preparation of perfluorocarbon emulsions either for manufacture at a manufacturing facility or by implementation of the vortexing/sonication protocol at the point of use.

Example 4. Production of Dodecafluoropentane—Phospholipid Nanoemulsions by Vortexing Combined Components in Glass Vials Followed by Ultrasonication A mixture of phospholipids DPPC (dipalmitoylphosphatidyl choline), DPPE-PEG-5000 (1,2-dipalmitoyl-sn-glycero-3-phosphoethanolamine-N-[monomethoxy poly(ethylene glycol) (5000)] and DPPE (1,2-dipalmitoyl-sn-glycero-3-phosphoethanolamine) was prepared at a concentration of 0.3% w/vol total phospholipids with DDFP (2% w/v) in a crimp-capped nominal 5 mL vial (actual total capacity 9 mL). The sealed vials were vortexed for at least 30 seconds upright and 30 seconds inverted and then subjected to sonication for 2, 8 or 16 min. The results for each sonication time are displayed in Table 7.

disruption of the phospholipid micelles and the formation of encapsulated nanodroplets. The scattering intensity of the sample aliquot from the 2 minute sonication was significantly increased when compared with the same size aliquot of the vortexed-only sample.

The substantially decreased Xi Sq and % SD are consistent with the formation of a Gaussian nanoparticle distribution similar to that obtained by high-pressure homogenization. Increased ultrasonication time (8 min and 16 min) brings the system closer to saturation values for the particle size distributions as evidenced by decreased IWMD, VWMD, % SD, IWCUM99%< and VWCUM99%<values. This data demonstrates that the utility of ultrasonication to produce submicron-sized encapsulated perfluorocarbon nanodroplets is not restricted to any particular class of surfactant but can be applied to produce encapsulated perfluorocarbon nanodroplets using different surfactant types particularly suited to specific applications.

Example 5. In-Line Real Time Particle Size Reduction of Out-of-Specification Emulsions An experiment was performed to determine if ultrasonication can be used in an in-line system for injection. A vial of out-of-specification DDFP-PTB emulsion was vortexed 30 seconds upright and 30 seconds inverted and allowed to stand 1 min. A 1 mL. Becton and Dickinson syringe fitted

TABLE 7

Vortexing and Sonication of Vials Containing DDFP and a Phospholipid Suspension to Produce Phospholipid Encapsulated Perfluorocarbon Nanodroplets

| Sonication time (min) | IWMD (nm) | VWMD (nm) | NWMD (nm) | SD (%) | IWCUM 99%< (nm) | VWCUM 99%< (nm) | Xi Sq |
|---|---|---|---|---|---|---|---|
| 0 | 292.1 | 232.3 | 50.8 | 59.3 | 972.8 | 773.8 | 1.26 |
| 2 | 395.6 | 451.8 | 201.3 | 41.4 | 950.7 | 1085.9 | 0.11 |
| 8 | 372.4 | 414.2 | 222.0 | 37.5 | 830.1 | 923.2 | 0.12 |
| 16 | 360.0 | 386.9 | 286.0 | 28.8 | 674.6 | 724.9 | 0.58 |

Vortexing the heterogeneous mixture of components provides a suspension whose sizing data (sonication time=0 min) is indicative of the presence of some encapsulated nanodroplets likely accompanied by a significant amount of phospholipid micelles (as evidenced by the small value of the NWMD) and perhaps and non-encapsulated fluorocarbon droplets. Another indicator of the nature of the vortexed mixture is a low scattering intensity when compared with the same sized sample aliquots of material from the sonicated vials.

Sonication for a short period (2 min.) provides IWMD, VWMD and NWMD that are characteristic of submicron-sized encapsulated perfluorocarbon nanodroplets. More specifically, the 4-fold increase in the NWMD indicates the with a 1.5" 22-gauge disposable needle was employed to sample a 0.3 mL aliquot of the vortexed material for particle sizing after the vortexing step by pressurizing the headspace with 0.5 mL of air followed by allowing the syringe to passively fill with the desired aliquot of the emulsion.

A 6 mL NormJect™ disposable plastic syringe (Henke Sass Wolf) fitted with a 1.5" 22-gauge Becton and Dickinson disposable needle was charged with 5 mL of air. The stopper of the vial was punctured from above and the vial was pressurized by injection of the air into the vial headspace. The entire assembly was inverted and the syringe was allowed to passively fill with 5 mL of the emulsion. The emulsion was then injected into the headspace of the inverted vial and the syringe again allowed to passively fill with 5 mL of the emulsion.

The needle was immediately removed from the syringe and the syringe was fitted with polypropylene tubing (⅛" o.d., 1/16" i.d.) employing a female 1/16" i.d. Luer Lock fitting-to-1/16" barb adaptor. The internal volume of the polypropylene tubing was 2.2 mL.

FIG. 1 shows an exemplary embodiment of equipment used for in-line ultrasonication of either an out of specification nanoemulsion or a coarse emulsion generated by vortexing of a glass vial of combined components of the nanoemulsion followed by aspiration of the coarse emulsion into a syringe. Syringe pump 120 is used to deliver at a controlled rate the syringe 110 contents into a coil of tubing that is immersed into ultrasonic cleaning bath 130. The length of the tubing and the speed setting on the syringe determine the residence time of the syringe contents in the tube and also the time for which ultrasonication is applied to the delivered syringe contents.

Figure 2:
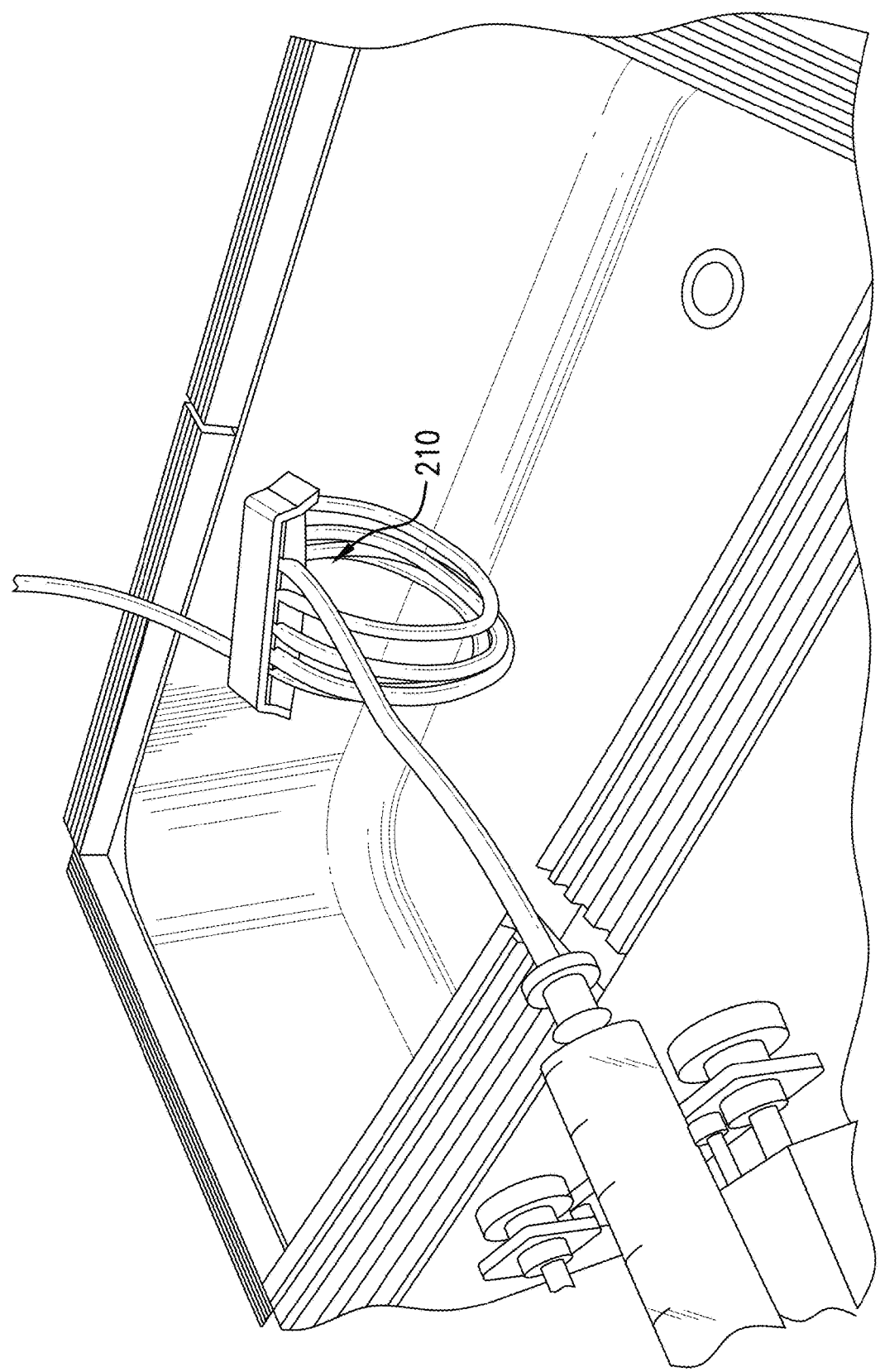
FIG. 2 shows an exemplary embodiment of the configuration of coiled tubing used for in-line sonication (or ultrasonication using an ultrasonic cleaner) of a coarse emulsion of fluorocarbon or perfluorocarbon and aqueous surfactant or an out of specification emulsion of fluorocarbon or perfluorocarbon and aqueous surfactant.
Figure 3:
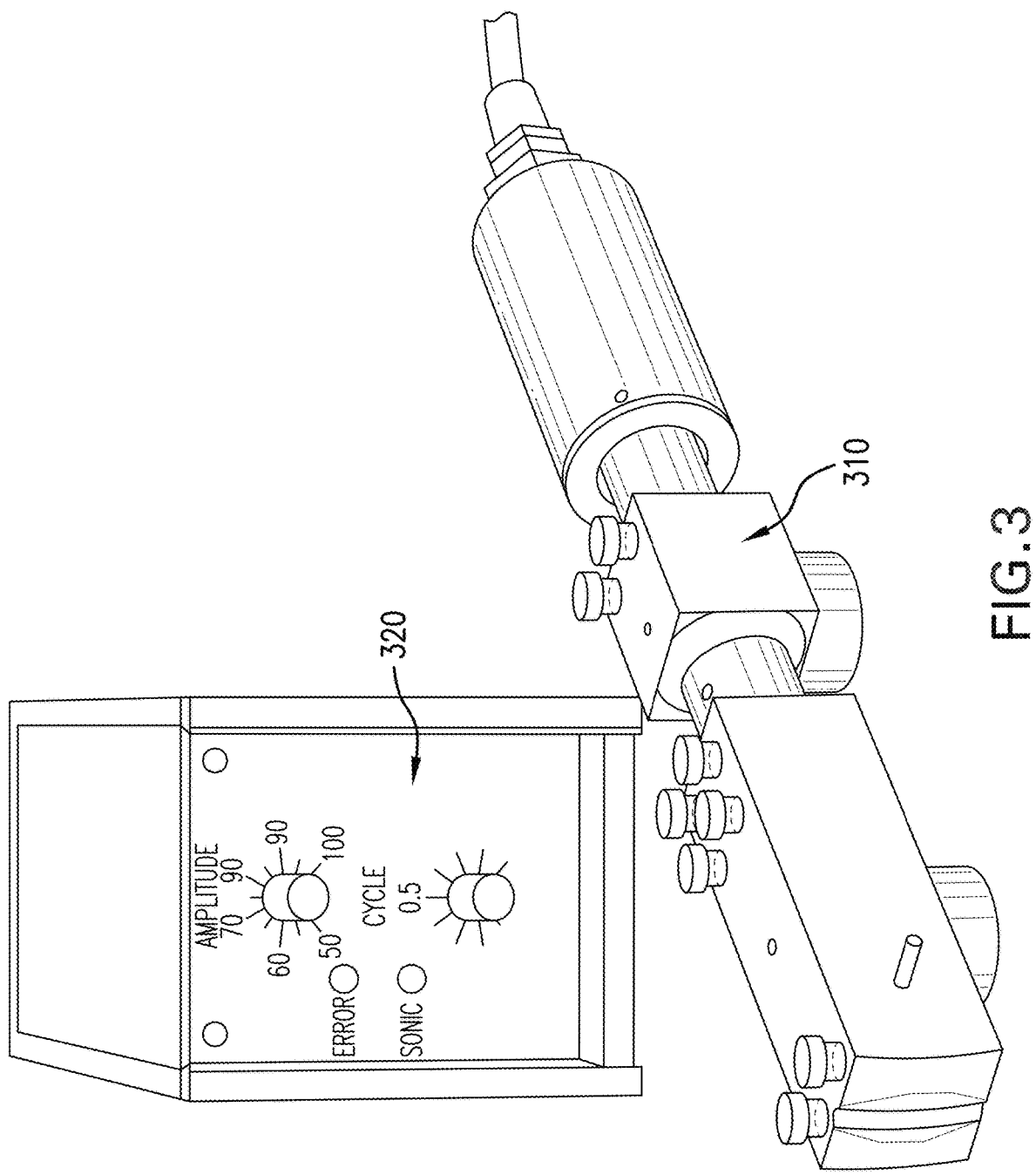
FIG. 3 shows an exemplary embodiment of the VialTweeter (Hielscher Ultrasonics GmbH, Teltow, Germany) powered by its companion ultrasonic processor UIS250v. This unit is capable of transmitting ultrasonic energy to a vial or a syringe or tubing with the correct suitably configured sonotrode. The power of the ultrasound can be varied using the ultrasonic processor, which can vary ultrasonication with respect to pulsing, amplitude and power for optimization of specific applications.
Figure 4:
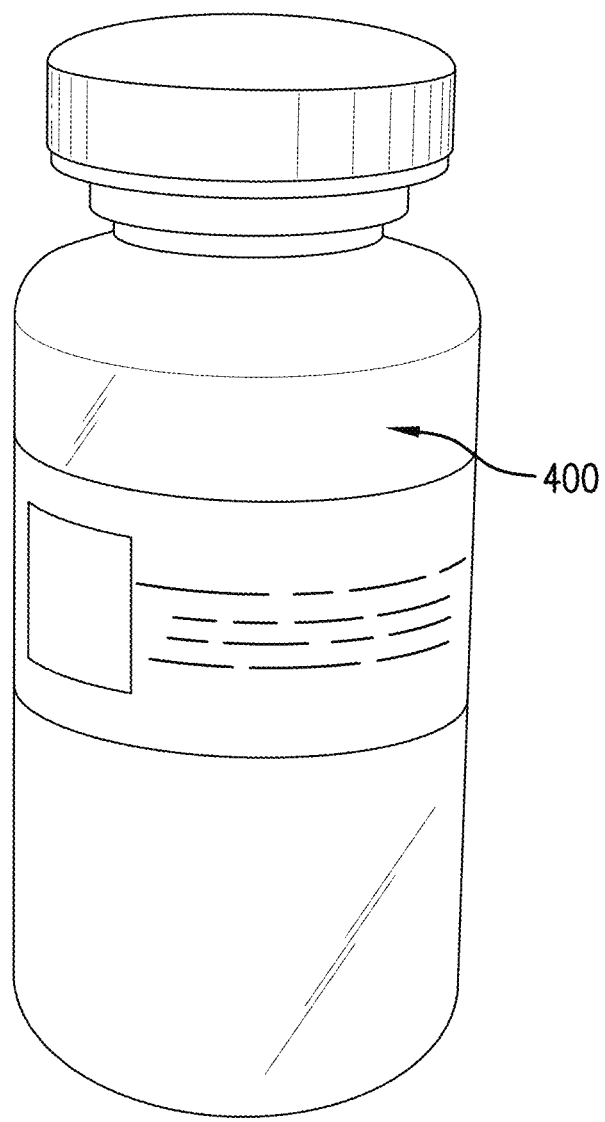
FIG. 4 shows an exemplary embodiment of a typical nominal 10 mL capacity vial of a nanoemulsion of perfluoropentane (2% w/v) and PEG-Telomer B surfactant (0.3% w/v) in phosphate buffered 30% aqueous sucrose solution.
Figure 5:
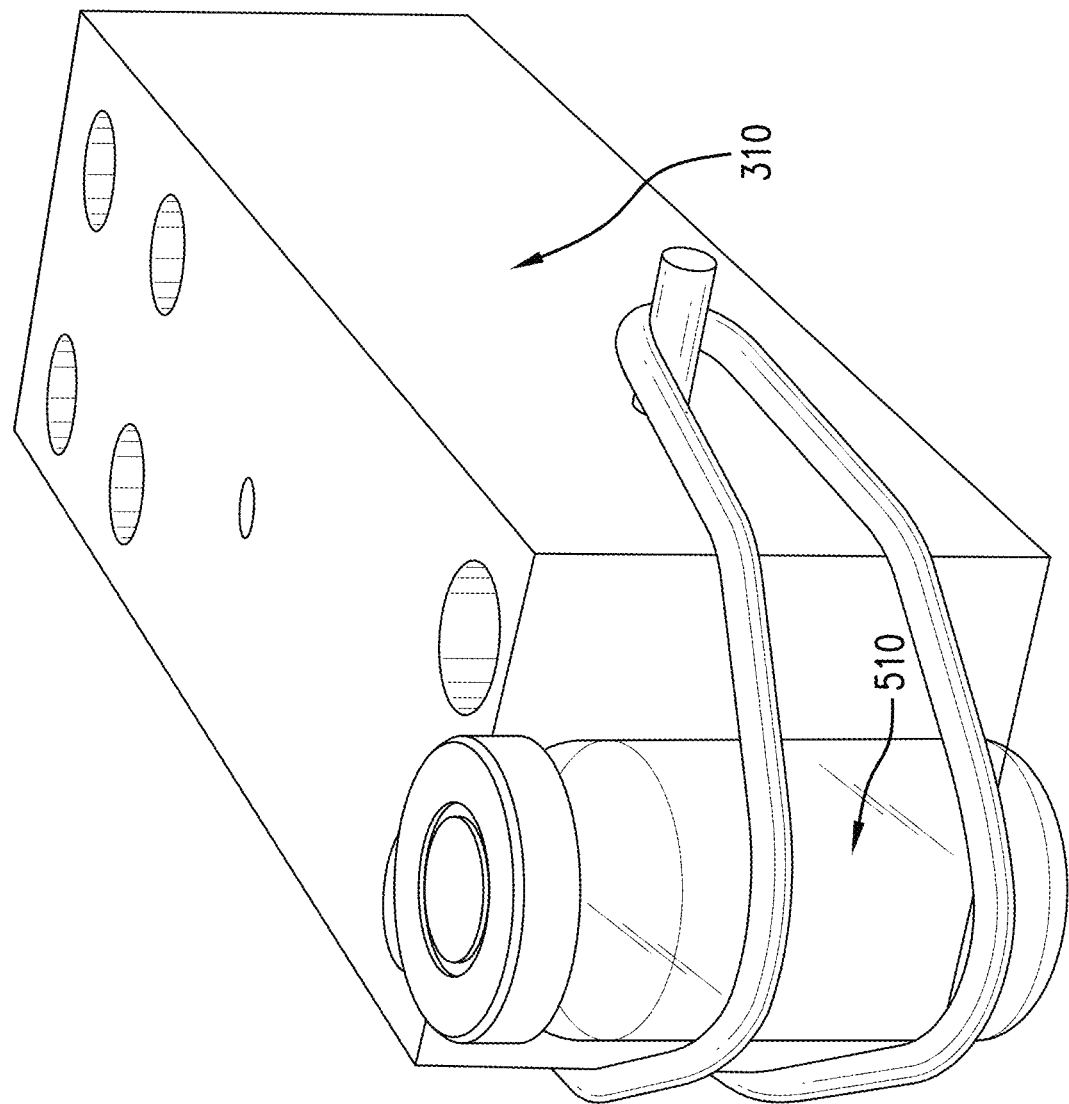
FIG. 5 shows an exemplary embodiment of a vial, which can have a volume of up to 50 mL, containing a solution to be ultrasonicated using the Vial Tweeter. The vial can be affixed to the end of the sonotrode fixture of the Vial Tweeter.

FIG. 2 shows an exemplary embodiment of the configuration of coiled tubing used for in-line sonication or ultrasonication (using a ultrasonic cleaner) of a coarse emulsion of fluorocarbon or perfluorocarbon and aqueous surfactant or an out of specification emulsion of fluorocarbon or perfluorocarbon and aqueous surfactant. In general practice the coiled tubing is completely immersed in the water of the bath. However, the when the coil is positioned wherein the axis of the coil perpendicular to the spiral of the coil is parallel to the bottom of the ultrasonic bath (as shown in this figure), the depth of immersion of the coil of tubing into the water of the ultrasound bath can be used to change the duty cycle of the process. If each loop of the series of loops that makes up the coil is half-immersed into the water of the ultrasonic bath this provides a 50% duty cycle, for example. This may be desirable because continuous ultrasonication may raise the temperature of the nanoemulsion to an unacceptable level. By using a shorter duty cycle the temperature of the prepared nanoemulsion can be controlled. If the coil of tubing is further or less immersed in the water bath of the ultrasonic cleaner the duty cycle is increased or decreased respectively and this constitutes a simple and expedient method for control of the duty cycle if required. In this manner the particle size parameters and the temperature of the prepared can be controlled.

Referring to FIGS. 1 and 2, the tubing was coiled in loops 210 (FIG. 2) about 2" in diameter resulting in an array of side-by-side loops which was held in place using a plastic hinge clip with grooves that allowed positioning of the tubing. The syringe was then placed in a Harvard Apparatus model 11 plus syringe pump 120. The syringe pump was set to a flow rate of 1 cc/min. The coiled tubing was completely immersed in the water bath of a VWR Aquasonic 75HT sonicator 130. The syringe pump was started and immediately thereafter sonication was initiated. The out-of-specification emulsion was exposed to sonication as it flowed through the looped tubing in the sonicator water bath. The sonicated material was collected into a vial kept at 10° C. The vial was immediately capped with a butyl rubber stopper until the material was sampled for particle sizing (~1 min after cessation of collection). Table 8 shows the particle size data obtained for the out-of-specification material post vortexing but pre-sonication and post vortexing and in-line sonication.

TABLE 8

Particle Size Data for Vortexing and In-Line Sonication of Out-of-Specification DDFP-PTB Emulsion

| Sample Description | IWMD (nm) | VWMD (nm) | NWMD (nm) | SD (%) | IWCUM 99%< (nm) | VWCUM 99%< (nm) | Xi Sq |
|---|---|---|---|---|---|---|---|
| ortexed - no sonication | 902.3 | 1091.5 | 610.0 | 43.6 | 2261.1 | 2753.3 | 0.04 |
| Vortexed followed by In-Line Sonication | 202.7 | 170.4 | 105.3 | 34.7 | 427.5 | 359.5 | 0.64 |

The technique described in this example provides DDFP-PTB nanoemulsion that displays particle size parameters displayed by material prepared by high-pressure homogenization (see Table 1). This shows that the highest quality materials can be obtained by the remedial process disclosed herein. Thus, nanoemulsion materials that have undergone particle size growth over substantial storage periods and exhibiting out-of-specification particle size parameters can be efficiently and effectively rectified using an in-line process.

Example 6. In-Line Real Time Preparation of DDFP-PTB Emulsion from Combined Components An experiment was performed to determine if in-line ultrasonication can provide DDFP-PTB emulsion by merely charging a vial with the components of the nanoemulsion, suspending the component mixture by vortexing followed by in-line sonication. This technique can allow injection of the nanoemulsion in immediate real time after its preparation in a just-in-time scenario.

A nominal 5 mL serum vial (actual volume 9 mL) was charged with Peg Telomer-B (24.4 mg) and 0.2 micron filtered 30% Sucrose in WFI (water for injection) (7.65 mL). Then chilled DDFP (0.179 g) was added using a 1 mL tuberculin insulin-dispensing syringe (essentially zero dead volume). The vial was immediately crimp-capped and vortexed for 1 min upright and 1 min inverted. The vial was allowed to stand 1 min then gently inverted 10×. A 0.3 mL aliquot was sampled for particle sizing as described in Example 5. Then, a 5 mL aliquot of the vortexed material was processed exactly as described in Example 5.

Table 9 displays the particle size data obtained for the component mixture post vortexing pre-sonication and post vortexing and in-line sonication.

TABLE 9

Particle Size Data for Vortexing and Sonication of Suspended Components of DDFP-PTB Emulsion

| Sample Description | IWMD (nm) | VWMD (nm) | NWMD (nm) | SD (%) | IWCUM 99%< (nm) | VWCUM 99%< (nm) | Xi Sq |
|---|---|---|---|---|---|---|---|
| Vortexed - no sonication | 1216.6 | 1855.3 | 449.2 | 65.3 | 4483.2 | 6736.3 | 0.37 |
| Vortexed followed by In-Line Sonication | 211.3 | 182.1 | 112.3 | 34.3 | 442.3 | 381.1 | 0.57 |

The preparation of DDFP-PTB nanoemulsion using the technique described in this example provided a nanoemulsion with particle size parameters displayed by material prepared by high-pressure homogenization (see Table 1). This demonstrates the effectiveness and utility of the in-line preparation of the emulsion.

Benefits of this technique include: (1) immediate preparation of highest quality material, (2) highly uniform quality of material, (3) storage of components either as a biphasic mixture in a vial or as separated components which are combined in real time so that each component can be stored under conditions for its maximum stability, (4) allowing storage of the more stable components (such as DDFP) without the need for refrigeration or other environmental controls, where possible, and (5) minimizing waste of material that may occur due to shelf life limitations of pre-formed emulsions stored for long periods.

Example 7. Production of DDFP Nanoemulsions Wherein the Bulk of DDFP is Reduced to Sub-100 nm Particles A 6 mL Henke Sass Wolf Normject disposable syringe fitted with dosage measuring clips (vol 5 mL) and a disposable 22 gauge needle was filled by aspiration with a 5.8 mL sample of an out-of-specification-nanoemulsion (OOSN) (2% DDFP w/v; 0.3% Peg-Telomer B w/v; 30% Sucrose w/v in aqueous 10 mM sodium phosphate buffer, pH 7). After aspiration of the sample the needle was removed and the Luer Lock of the syringe was sealed to atmosphere with a dead-end cap fitting. The assembly was positioned left-right and front-rear centered in the bath of a VWR Aquasonic HT75 ultrasonic cleaner with the Luer Lok of the syringe facing the bottom of the water tank and with the long axis of the syringe perpendicular its bottom. The fluid level of the syringe was 0.5" below the water level of the bath. Sonication was conducted for 2 min. at 25° C., the syringe was removed from the bath and was allowed to stand at ambient temperature for 30 min.

This experiment was performed on two more samples for a total of three trials. Data for particle size parameters for these samples appears in Table 10. Particle size parameters were obtained using a PSS Nicomp 380 DLS submicron particle-sizing instrument.

TABLE 10

Sonication of Out-of-Specification DDFP Nanoemulsion in a Disposable Syringe Provides High Quality Nanoemulsion

| Sample (Sonication time-min) | IWMD (nm) | VWMD (nm) | NWMD (nm) | % Std Dev | IWCum 99%< (nm) | VWCum 99%< (nm) | VWCum 75%< (nm) | Xi Sq |
|---|---|---|---|---|---|---|---|---|
| OOSN (0) | 870.8 | 1044.1 | 599.3 | 42.6 | 2141.2 | 2567.5 | | 0.04 |
| 1 (2) | 112.6 | 98.5 | 84.0 | 22.6 | 185.6 | 162.4 | 111.8 | 0.35 |
| 2 (2) | 110.5 | 84.6 | 61.7 | 31.6 | 219.2 | 167.7 | 99.5 | 0.68 |
| 3 (2) | 116.4 | 89.4 | 65.0 | 31.6 | 230.8 | 177.3 | 105.2 | 0.22 |
| Average | 113.2 | 90.8 | 70.2 | 28.6 | 211.9 | 147.8 | 105.4 | 0.42 |
| SD | 3.0 | 7.1 | 12.0 | 5.2 | 23.5 | 43.0 | 5.11 | 0.24 |
| RSD (%) | 2.6 | 7.8 | 17.1 | 18.2 | 11.1 | 29.1 | 4.85 | 56.9 |
| % Reduction by sonication | −87.0 | −91.3 | −88.3 | −32.9 | −90.1 | −94.2 | | N/R |

Very large particle size parameters were found for the OOSN, as shown in the OOSN (0) entry of Table 10. Inspection of the data indicates that the IWMD, VWMD and NWMD for the in-syringe sonicated OOSN were well within specification. The values were approximately 50% of those observed for material obtained by sonication of OOSN in glass vials or even fresh material obtained using high-pressure homogenization as the emulsification technique (see Table 1). This unexpected result indicates that sonication in the plastic disposable syringe resulted in nanoemulsions of particle size that were not accessible using high-pressure homogenization at average pressure of 7250 psi or by sonication of the precursor OOSN in glass vessels at 40 KHz at total power of 75 watts (Aquasonic HT75 ultrasonic cleaner).

Sonication of the material in the plastic disposable syringe quickly provides nanoemulsions of DDFP where the mean particle size of the majority of the mass of the input DDFP is less than 106 nm. This was demonstrated by the average Volume Weighted Cumulative 75% Distribution<value of 105 nm. Such emulsions are useful for special applications where smaller particles may be more suitable than typical perfluorocarbon nanoemulsions obtained by high-pressure homogenization.

Table 11 displays comparative data for DDFP nanoemulsions produced by high-pressure homogenization, combination of separate components in a glass vial followed by vortexing and sonication, vortexing of OOSN in a glass vial followed by sonication and vortexing OOSN in a glass vial followed by transfer of the material to a disposable plastic syringe and sonication of the syringe oriented with its long axis perpendicular to the floor of the bath.

TABLE 11

Comparison of Particle Size Parameters for Sodium Phosphate Buffered DDFP (2% w/v)-Peg-Telomer B (0.3% w/v)-Sucrose (30% w/v) Nanoemulsions Produced by High-Pressure Homogenization and Sonication

| Method for Preparation of DDFP Nanoemulsions | IWMD | VWMD | NWMD | Std Dev (%) | IWCUM 99%< | VWCUM 99%< | $Xi^2$ |
|---|---|---|---|---|---|---|---|
| High-pressure homogenization of DDFP and surfactant at 7250 psi followed by dissolution in 32% sucrose solution. | 232.2 | 212.0 | 132.2 | 33.3 | 476.4 | 437.1 | 0.34 |
| Combine components and crimp cap glass vial, vortex, sonicate 2 min. | 202.3 | 170.4 | 106.0 | 34.5 | 425.1 | 358.1 | 0.20 |
| Vortex OOS material in glass vial, sonicate 2 min. | 219.6 | 188.3 | 105.9 | 36.7 | 481.1 | 413.0 | 0.26 |
| Vortex OOS material in glass vial, aspirate into plastic disposable syringe, sonicate filled syringe in vertical orientation 2 min. | 113.2 | 90.8 | 70.2 | 28.6 | 211.9 | 147.8 | 0.42 |

The greatest difference in particle size parameters was found when the plastic syringe was the vessel in which the sonication was conducted. Thus, where mean particle diameter in the sub-100 nanometer range is desired, sonication of coarse emulsions in a plastic syringe can be employed to rapidly and efficiently generate them. This allows the on-demand preparation of high quality nanoemulsions for use in emergency situations by first responders.

Example 8. Production of Perfluorocarbon Nanoemulsions by Sonication of a Syringe Containing Combined Components: Control of Particle Size of in-Syringe Sonicated Perfluorocarbon Nanoemulsions Example 7 above illustrated how to produce PFC nanoemulsions having sub-100 nm particle size parameters for the bulk of the input DDFP after sonication of the vortexed mixture of combined components in the syringe. It has been observed that shortening the sonication time to even 1 minute does not provide perfluorocarbon nanoemulsions typical of those obtained using high-pressure homogenization. However, it has been discovered that sonication (in the syringe) of a vortexed mixture of combined components wherein the relative amount of PFC, for example DDFP, is increased with respect to the other components in the mixture easily provided the PFC nanoemulsion which has particle size parameters typical of a nanoemulsion produced by high-pressure homogenization except that the emulsion is now increased in concentration of surfactant-stabilized DDFP. This allows on-demand production of the desired emulsion type in a more compact and economical format with respect to total volume and use of sucrose and surfactant per unit of DDFP emulsified.

An illustrative example is where the DDFP concentration is raised to 4% w/v while the concentration of the rest of the components remains the same; hence DDFP 4% w/v, Peg-Telomer B surfactant remaining at 0.3% w/v, sucrose remaining at 30% w/v and phosphate buffer controlled at 10 mM. Nominal 5 mL capacity vials (actual total volume 9.0 mL) containing 7.77 mL of this mixture were vortexed for 30 seconds upright and 30 seconds inverted. Then, the mixture was aspirated into a Henke Sass Wolf Normject™ disposable plastic syringe fitted with a 1.5", 22-gauge disposable needle and dosing clips until the syringe was entirely filled. The needle was removed and the Luer Lok of the syringe was sealed off using a dead end cap fitting. The syringe was positioned centered left-right and front-rear in the tank of the VWR Aquasonic 75HT ultrasonic cleaning bath with the long axis vertical to the bottom of the tank as described in Example 7.

Sonication was conducted for 3 min., the syringe was removed from the bath and an aliquot of the contents of the syringe was employed for submicron particle sizing. Results for three trials are given in Table 12.

The sonication of combined components in the syringe wherein the relative concentration of DDFP (4% w/v) vs the other components was double that in a standard 2% DDFP nanoemulsion provides a simple, on-demand route to perfluorocarbon nanoemulsions with particle size parameters characteristic of the standard 2% w/v DDFP nanoemulsion produced by high pressure homogenization (see Table 1). This reduces the volume needed by 50%, and reduces needed amounts of the surfactant, the sucrose, and aqueous buffer also by 50% while providing freshly prepared material of the required specification.

TABLE 12

Particle Size Parameters for a DDFP 4% w/v, PTB 0.3% w/v, Sucrose 30% w/v, 10 mM Sodium Phosphate Buffer Nanoemulsion Produced by Vortexing Combined Components in a Vial Followed by Transfer to, and Sonication in, a Plastic Disposable Syringe

| Sample No. | IWMD (nm) | VWMD (nm) | NWMD (nm) | Std Dev (%) | IWCum 99%< (nm) | VWCum 99%< (nm) | Xi Sq |
|---|---|---|---|---|---|---|---|
| 1 | 225.2 | 211.1 | 157.4 | 27.2 | 408.3 | 382.7 | 0.28 |
| 2 | 233.2 | 218.7 | 148.7 | 30.3 | 450.5 | 422.5 | 0.21 |
| 3 | 236.7 | 215.8 | 123.7 | 35.4 | 506.3 | 461.5 | 0.22 |
| Average | 231.7 | 215.2 | 143.3 | 31.0 | 455.0 | 422.2 | 0.24 |
| SD | 5.9 | 3.8 | 17.5 | 4.1 | 49.2 | 39.4 | 0.04 |
| RSD (%) | 2.5 | 1.8 | 12.2 | 13.4 | 10.8 | 9.3 | 16.00 |
| Typical Values for 2% DDFP Nanoemulsion from High Pressure Homogenization | 232.2 | 212.0 | 132.2 | 33.3 | 476.4 | 437.1 | 0.34 |

Prophetic Example 1. Ultrasonication of a Single or of Multiple Vials Using a the Vial Tweeter Wherein the Sonic Energy is Transmitted to the Vials by Direct Contact This example shows how multiple or single sealed vials may be sonicated without a water bath using a piezoelectric device. An example of such a device is a VialTweeter (Hielscher Ultrasonics GmbH, Teltow, Germany), which can be used to expose multiple vials to ultrasound energy at a time. A water bath is not necessary to transmit the ultrasound energy into the sealed vial.

FIG. 3 shows an exemplary embodiment of the VialTweeter 310, which is powered by the ultrasonic processor UIS250v 320 (250 watts, 24 kHz). This unit is capable of transmitting ultrasonic energy to a vial or a syringe or tubing with the correct suitably configured sonotrode. The power of the ultrasound can be varied using the ultrasonic processor, which can vary ultrasonication with respect to pulsing, amplitude and power for optimization of specific applications. The VialTweeter delivers up to 10 watts to each of the six vials in its high intensity part and up to 5 watts to the two vials placed in its low intensity part.

FIG. 4 shows an exemplary embodiment of a typical nominal 10 mL capacity vial of NVX-108, a nanoemulsion of DDFP (2% w/v) and PEG-Telomer B surfactant (0.3% w/v) in phosphate buffered 30% aqueous sucrose solution. Vial 400 contains NVX-108. In certain embodiments, vial 400 is neither constructed nor arranged to cause reflection of acoustic energy in vial 400, or to form a secondary focal zone within vial 400.

Pre-filled, sealed vials can be placed into the VialTweeter to either decrease the size of emulsion that has gone out-of-specification or to prepare a finished emulsion from the starting materials that are contained within the sealed vial. The VialTweeter is made to hold vials of 12×32 mm or 15×45 mm. Larger vials, up to 50 mL can be attached to the end of the VialTweeter.

FIG. 5 shows an exemplary embodiment of a vial, which can have a volume of up to 50 mL, containing a solution to be ultrasonicated using the Vial Tweeter. The vial 510 can be attached to VialTweeter 310 (FIG. 3). This may represent vial 400 (FIG. 4) of NVX-108, or a pre-filled syringe. This can also represent a vial of an out of specification emulsion of NVX-108 or a coarse emulsion of the components used to prepare NVX-108 that has not yet been subjected to high pressure homogenization or any processing to convert the coarse emulsion into the desired nanoemulsion. In certain embodiments, vial 510 is neither constructed, nor arranged, to cause reflection of acoustic energy in vial 510, or to form a secondary focal zone within vial 510.

Prophetic Example 2. Sonication of Pre-Filled Syringes with VialTweeter or Other Systems Employing Power Supplies and a Transducer of an Array of Transducers Capable of Delivering Ultrasonic Energy This example shows how a VialTweeter 310 can be used to sonicate pre-filled syringes and how a power injector or syringe pump can be used to expose material to sonication while it is injected, e.g., into a patient.

FIG. 6A shows an exemplary embodiment of the Vial Tweeter with a sonotrode used for delivering ultrasound to a small volume sample.

The UIS250v 320 (FIG. 3) can be used for the very intense sonication of one single vial. The Sonotrode VT24d10 610 is designed to deliver up to 15 watts into a single vial. Sonotrodes for various vial diameters are available. Instead of a vial, a syringe, as shown below, can be fitted into the Sonotrode.

FIG. 6B shows an exemplary embodiment of a pre-filled syringe 620 containing a coarse fluorocarbon or perfluorocarbon surfactant emulsion or out of specification emulsion. The pre-filled syringe 620 can be fitted into the hole on the end of the Sonotrode and the positioning of the syringe surface with contacts the Vial Tweeter can be controlled such that the syringe contents 625 are in the zone where the Vial Tweeter generates the ultrasonic energy.

A source of ultrasound, for example a suitably configured sonotrode of the Vial Tweeter can be affixed to the syringe in the region occupied by the coarse fluorocarbon or perfluorocarbon surfactant emulsion or out of specification emulsion 625 and ultrasonication can be conducted prior to injection or during injection depending on the exact position of the sonotrode. It is understood that if the plunger is retracted and the coarse fluorocarbon or perfluorocarbon surfactant emulsion or out of specification emulsion 625 occupies a larger fraction of the interior of the syringe that the sonotrode can be affixed to the syringe on any part where the ultrasound can be transmitted with sufficient efficiency to provide the final nanoemulsion with the desired particle size.

Figure 6A:
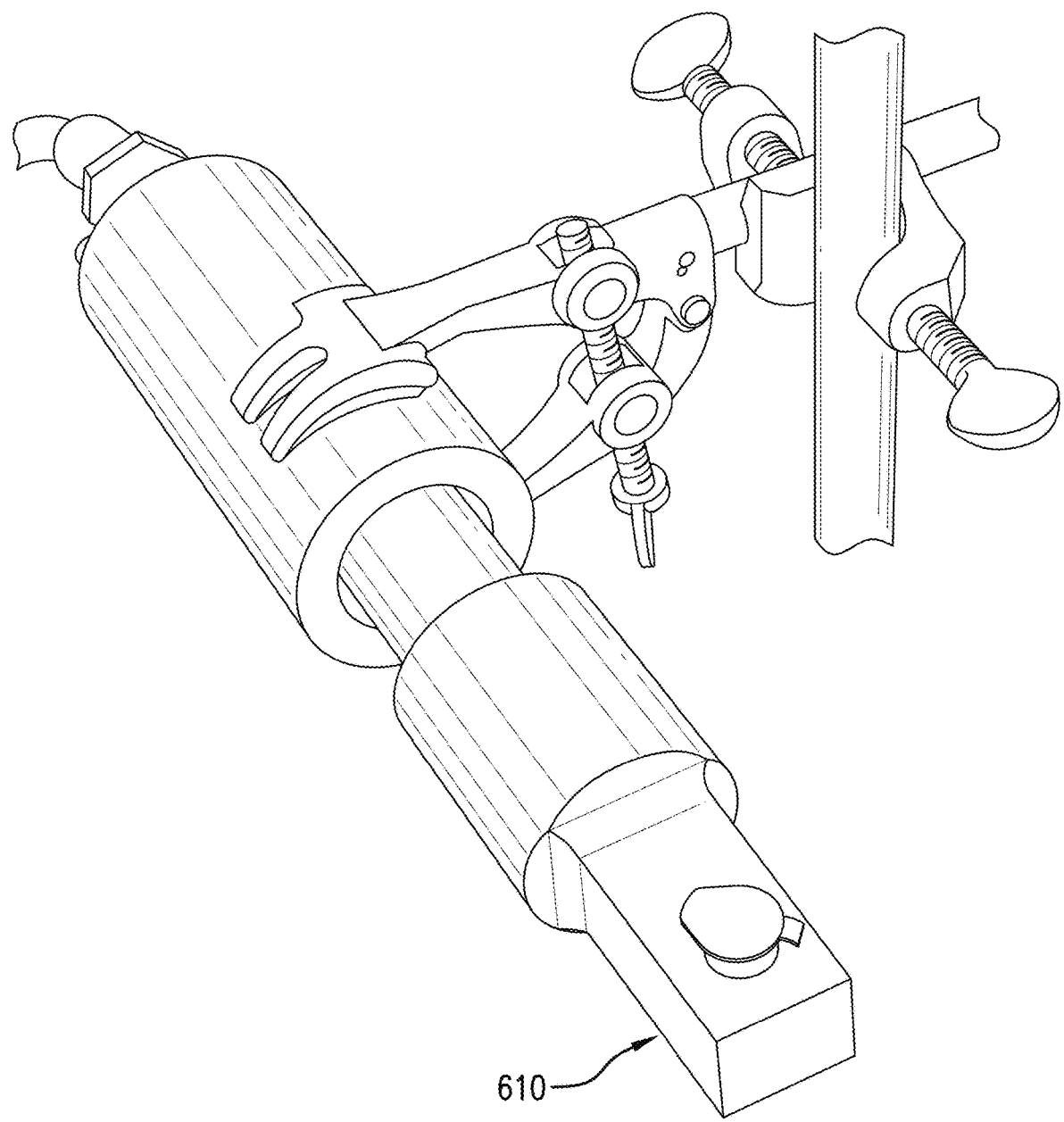
FIG. 6A shows an exemplary embodiment of the Vial Tweeter with a sonotrode used for delivering ultrasound to a small volume sample.
Figure 6B:
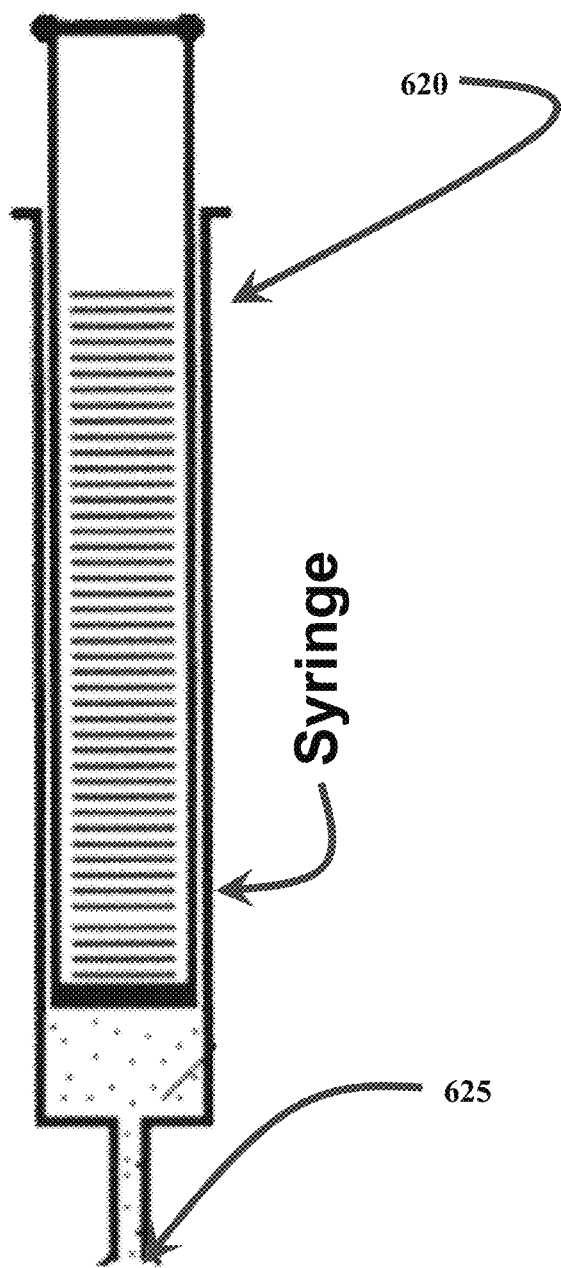
FIG. 6B shows an exemplary embodiment of a pre-filled syringe containing a coarse fluorocarbon or perfluorocarbon surfactant emulsion or out-of-specification emulsion. A source of ultrasound can be affixed to the syringe in the region occupied by the coarse fluorocarbon-surfactant emulsion or perfluorocarbon-surfactant emulsion or out of specification emulsion. Ultrasonication can be conducted prior to injection or during injection depending on the exact position of the sonotrode.
Figure 6C:
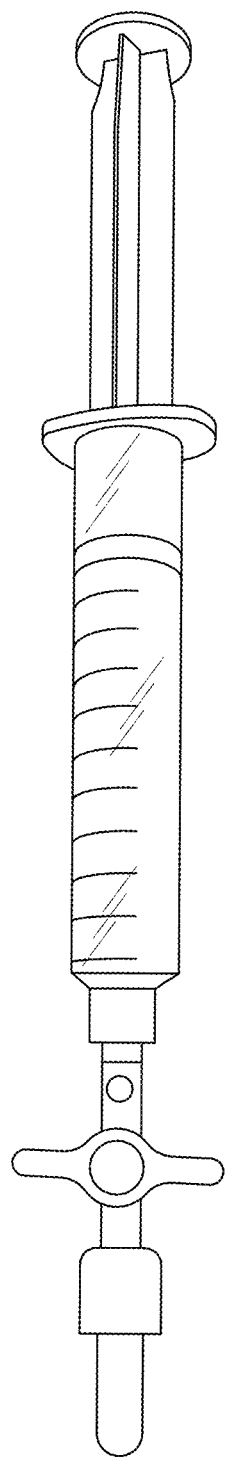
FIG. 6C shows an exemplary embodiment of a plastic disposable syringe filled with either a coarse emulsion of a fluorocarbon or perfluorocarbon and a surfactant or an out-of-specification emulsion of a fluorocarbon or perfluorocarbon and a surfactant which is ready to be ultrasonicated in a ultrasonic water bath in order to provide a fluorocarbon or perfluorocarbon surfactant nanoemulsion of the correct particle size.

Referring to FIG. 6C, when a pre-filled syringe is fitted into the Sonotrode, the syringe is ideally attached to a syringe pump or a power injector. A PC can monitor the power of the ultrasonic processor and the PC can control the syringe pump or power injector. The syringe pump or power injector will only be activated once the syringe, outflow chamber or tubing has been exposed to pre-specified intensity and duration of power.

Preferably the syringe is oriented vertically with the outlet of the syringe pointing down. The syringe may be oriented at different degrees from the horizontal to the vertical positions. The vertical orientation or variation, thereof, is so that any adventitious larger microbubbles, or adventitious gas will float to the top and not be injected into the patient.

Figure 6D:
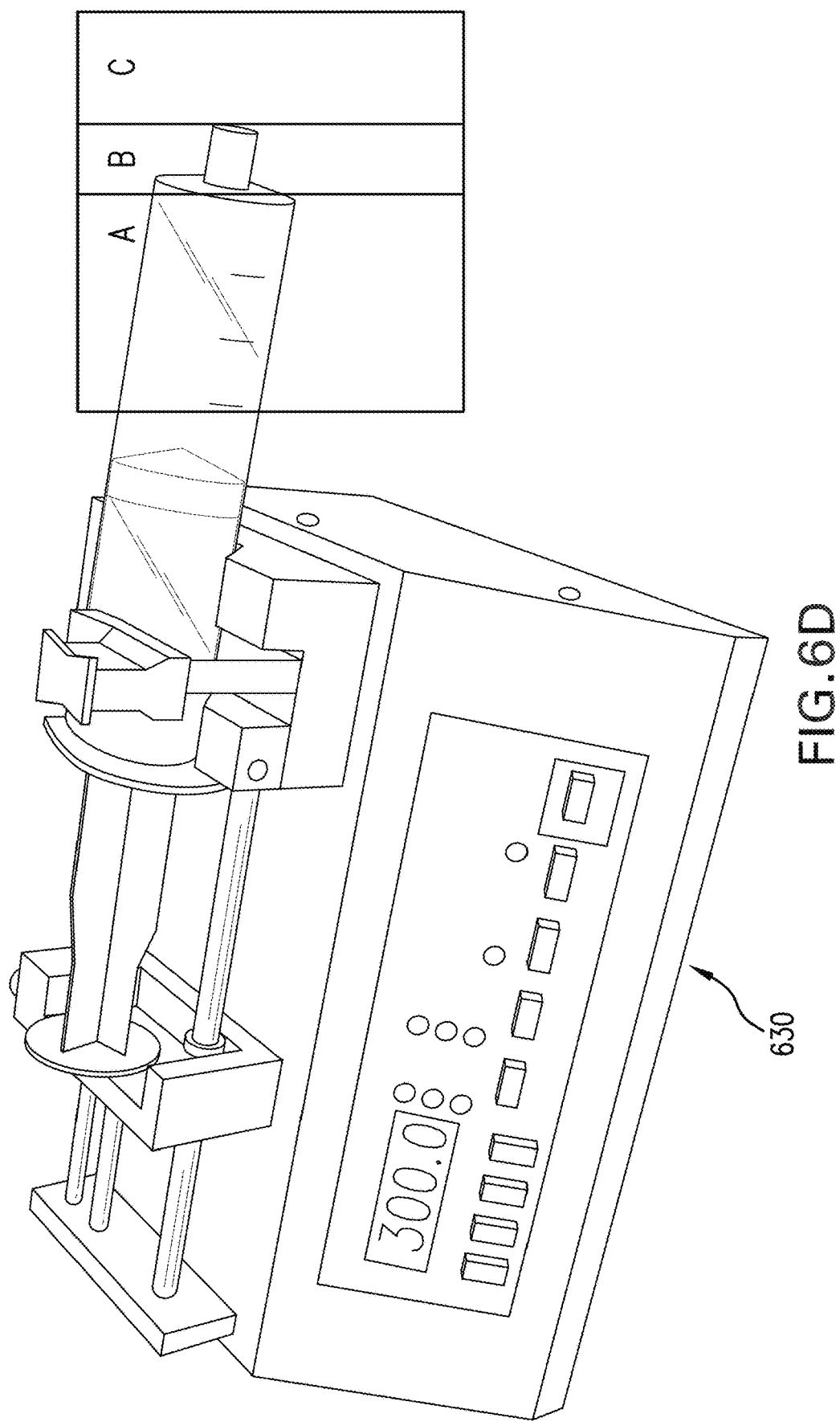
FIG. 6D shows an exemplary embodiment wherein a syringe containing a coarse emulsion of a fluorocarbon or perfluorocarbon and a surfactant or an out-of-specification emulsion of a fluorocarbon or perfluorocarbon and a surfactant is affixed to a syringe pump.

The illustrated embodiment of FIG. 6D illustrates syringe pump-NE-300-U 630 with a pre-filled syringe attached. The boxed areas A, B and C are zones wherein a suitably configured sonotrode of the Vial Tweeter can be attached in order to allow ultrasonication of the above mentioned coarse or out of specification emulsion. Zone A is the syringe barrel, Zone B is the area distal to the syringe barrel where the product has exited the syringe barrel and Zone C is where a sonotrode or other source of ultrasound may be affixed using an appropriate appliance staged before the tubing or tubing needle assembly that delivers the processed emulsion to the patient. Variation of the speed of delivery, the ultrasound power and duty cycle can be employed to provide nanoemulsions whose particle size is optimized for the particular application.

The illustrated embodiment of FIG. 6D illustrates syringe pump-NE-300-U 630 with a pre-filled syringe attached. Note how a significant length and also the end of the syringe barrel and the syringe is exposed and one skilled in the art would recognize that the syringe may be fitted into the end of the VialTweeter having a suitably configured sonotrode. By modifying the support for the housing of the pump, the syringe can be employed in a vertical or angled position with the tip of the syringe barrel pointing down. Note also that the contact point between the Vial Tweeter can be along the syringe barrel (FIG. 6D-Zone A) or at the area where the syringe contents exit the barrel (FIG. 6D—Zone B) or at a point further distal from the area where the contents of the syringe exit the syringe (FIG. 6D—Zone C). The Vial Tweeter is not the only system for ultrasonication that can be employed to deliver ultrasound in the configuration shown in FIG. 6D. Also of utility in the regard can be arrays of small transducers that may be assembled into ring shapes or cone shapes. Particularly, piezoelectric micromachined ultrasound transducers (PMUT) can be deployed to prepare arrays of transducers that can conform to the shape of any surface of the exterior of the syringe demarked by the Zone A, Zone B or Zone C. (Qiu et al. 2015 Sensors 15, 8020-8041.)

Figure 7A:
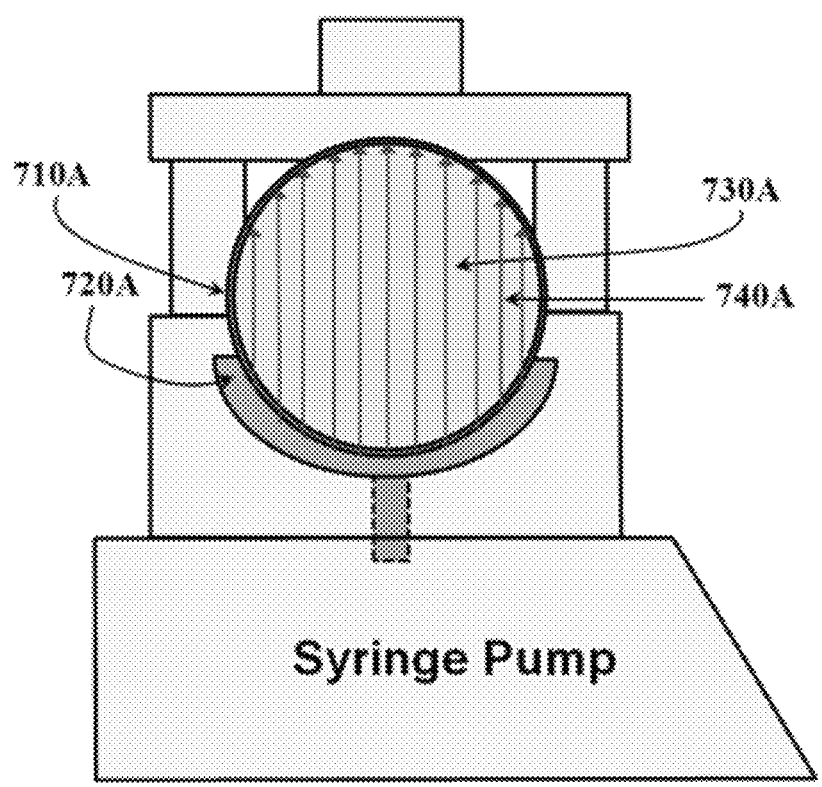
FIG. 7A shows an exemplary embodiment of a syringe fitted to a transducer, which itself is integrated into a syringe pump wherein the source of ultrasound is the integrated transducer.

Referring now to FIG. 7A, syringe 710A, containing DDFP nanoemulsion 730A, is positioned in contact with a piezoelectric transducer 720A. Ultrasound 740A is applied to the DDFP emulsion 730A in syringe 710A. The transducer 720A may subtend different fractions of the circumference of the barrel of syringe 710A for example from as little as 1% to 100%. In certain embodiments, the transducer 720A and a power supply for transducer 720A is integrated with the syringe pump disclosed herein so that flow rate is controlled while ultrasound power is applied to the contents in the syringe. In another embodiment the transducer 720A can be integrated into the syringe pump while a separate power supply may be employed to power the transducer 720A.

Figure 7B:
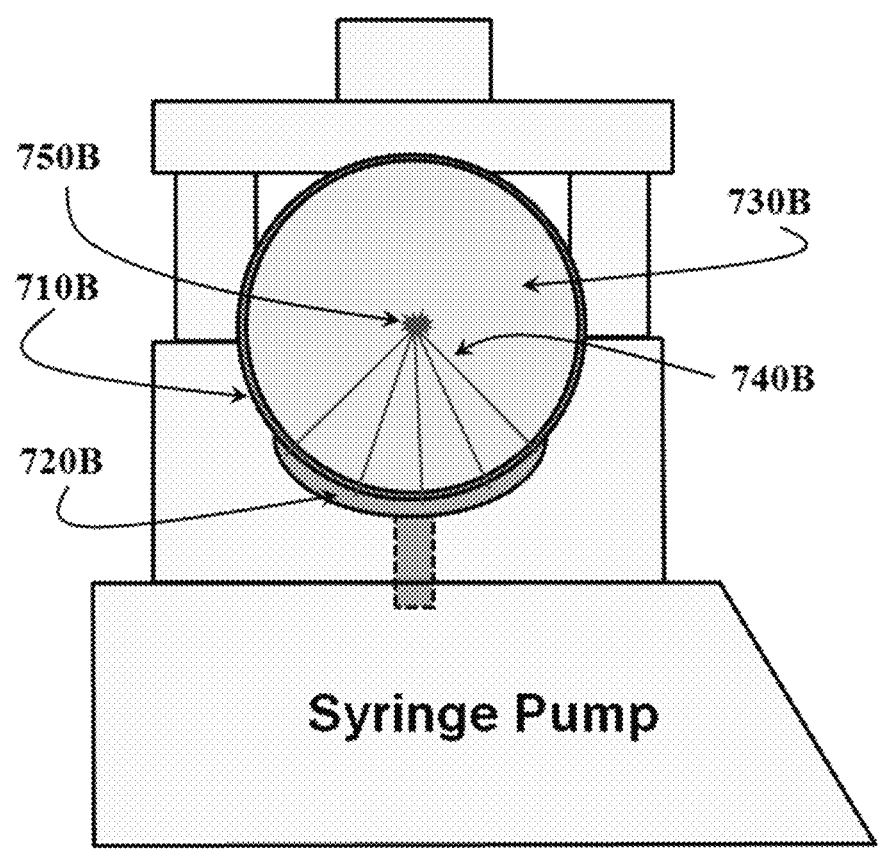
FIG. 7B shows an exemplary embodiment of a syringe fitted into a focusing ultrasound transducer which itself is integrated into a syringe pump wherein the source of focused ultrasound is the integrated transducer.

In FIG. 7B, syringe 710B containing coarse DDFP emulsion or out of specification DDFP emulsion 730B, is positioned in contact with a focused piezoelectric transducer 720B. Focused ultrasound 740B is applied to the coarse DDFP emulsion or out of specification DDFP emulsion 730B in syringe 710B. The ultrasound energy is focused at a point in the coarse DDFP emulsion or out of specification DDFP emulsion 730B that is indicated by the focal point 750B. Note that the focal point 750B does not have to be in the center of the solution. The focused transducer 720B may subtend different fractions of the circumference of the barrel of syringe 710B, for example from as little as 1% to 100%. In certain embodiments, the transducer 720B and a power supply for transducer 720B is integrated with the syringe pump disclosed herein so that flow rate is controlled while ultrasound power is applied to the contents in the syringe. In another embodiment the transducer 720A can be integrated into the syringe pump while a separate power supply may be employed to power the transducer 720A.

Figure 8:
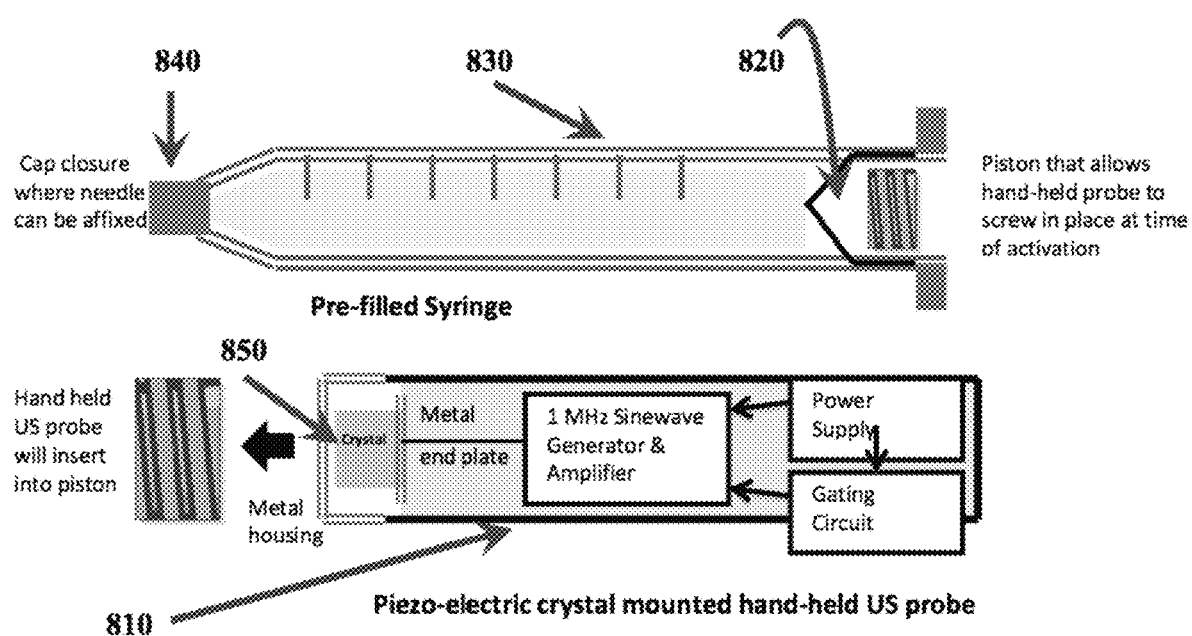
FIG. 8 shows an exemplary embodiment of a pre-filled syringe system that has a piston assembly into which a plunger containing an integrated transducer can be inserted. This allows ultrasonication of an out of specification emulsion of a fluorocarbon or perfluorocarbon and a surfactant or a coarse emulsion of a fluorocarbon of perfluorocarbon and a surfactant before delivery to a patient.

Prophetic Example 3. Sonication of Pre-Filled Syringes Using Custom-Made Integrated Transducer FIG. 8 shows how a custom-made sonication device may be constructed to adjust the size of an emulsion. FIG. 8 shows an exemplary embodiment of a pre-filled syringe system that has a piston assembly into which a plunger containing an integrated transducer can be inserted. This allows ultrasonication of an out of specification emulsion of a fluorocarbon or perfluorocarbon and a surfactant or a coarse emulsion of a fluorocarbon of perfluorocarbon and a surfactant before delivery to a patient.

A transducer or a hand held probe assembly 810 is affixed to a suitably constructed piston 820 of the syringe 830 to apply ultrasound energy to the base of the syringe through the acoustically transparent piston 820. The cap 840, forms a liquid and gas impermeable barrier at the end of the syringe. The cap 840 may comprise a luer lock or other valve.

Note that the contents in the syringe may be under pressure as the syringe may be stored at temperatures above the boiling point of the fluorocarbon or perfluorocarbon, for example, perfluoropentane, if used in harsh environments. The syringe, 830, may comprise glass or plastic material but is necessarily impermeable to liquid and gas. The syringe is filled with an emulsion or mixture of fluorocarbon, surfactant(s) and excipients. The piston 820 is designed to be pressure resistant and to prevent the gas and liquid to escape from the syringe under pressure that may exist due to the volatile nature of the fluorocarbon.

The interface between the piston 820 and the interior of the syringe barrel may comprise completely or in part of pharmaceutical rubber, silicone, or theromoplastic elastomer or a mixture thereof. The section of the piston 820 that contacts the syringe contents on its exterior and the transducer or piezoelectric device of the ultrasound probe on its interior may consist of stainless steel or other suitable material such as ceramic or other material that can transmit the applied ultrasound energy to the syringe contents with an efficiency that provides the nanoemulsion with the desired properties within the time limits set out in the specification herein.

The piston is designed to enable the hand-held ultrasound probe 810 to insert into its base. The ultrasound probe 810 comprises a piezoelectric transducer or mechanical vibration device 850 that makes contact with the interior of the piston 820 and transmits the ultrasound energy through the piston 820 into the fluid within the syringe. A sine wave generator (e.g., 1 MHz) and power supply, gating circuit and amplifier may be used to power the piezoelectric crystal or mechanical vibration device. Ideally this is all integrated into the detachable syringe plunger. The power supply can be a battery, preferably rechargeable and thereby reusable but may be provided as a single use device. Note that the circuit may be integrated with the gasket which will remain sealed to the end of the syringe barrel and immovable until a requisite duration of sonication (mechanical vibration) and pre-specified power have been delivered to the syringe. In so doing the integrated circuit can be used to ensure safety of the product as it can only be injected after sufficient power have been delivered to the contents of the syringe. Note that the ultrasound probe 810 rather than being a hand held device can also be integrated into a power injector device for use in hospital and operating room environments.

Prophetic Example 4. Treatment of Battle-Field Trauma Victim

A soldier suffers a blast injury with massive blood loss as well as traumatic brain injury. The paramedic obtains a prefilled syringe of 5% weight volume DDFPe from his backpack. The material appears layered and white opaque. The paramedic shakes the syringe vigorously by hand. He obtains the transducer from his backpack and screws it into the end of the syringe mating the piezo-electric transducer to the back of the gasket. The transducer engages automatically and imparts the requisite amount of ultrasound energy to the syringe. After exposure of sufficient ultrasound energy the material within the syringe appears translucent and uniform. A luer lock is affixed to the end of the syringe and a needle to that, covered by a housing. The paramedic removes the housing covering the needle and places the needle within a vessel (note that intra-osseous injection may also be used). The luer lock is opened and the paramedic presses the plunger (which may also contain the transducer) and delivers a dose of 0.25 mL/kg of 5% w/vol DDFPe, enough to treat a case of exsanguination.

While the preferred embodiments of the present invention have been illustrated in detail, it should be apparent that modifications and adaptations to those embodiments may occur to one skilled in the art without departing from the scope of the present invention.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the following description, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A method for reducing particle size of a perfluorocarbon nanoemulsion, wherein the perfluorocarbon emulsion is enclosed in a sealed vial or pre-filled syringe and is out-of-specification due to growth of particle size, the method consisting of applying sonication or ultrasonication to the perfluorocarbon emulsion for a time duration sufficient to adjust the particle size of the perfluorocarbon emulsion to a pre-selected value, wherein the perfluorocarbon nanoemulsion comprises one or more phospholipids and the perfluorocarbon is dodecafluoropentane having a concentration from about 2% w/vol to about 10% w/vol, wherein the mean particle size of the perfluorocarbon nanoemulsion is greater than about 1 micron prior to exposure to sonication or ultrasonication and less than about 500 nm after exposure to sonication or ultrasonication.

2. The method of claim 1, wherein the ultrasound is characterized by a frequency from about 10 KHz to about 10 MHz.

3. The method of claim 2, wherein the perfluorocarbon emulsion comprises a mixture of three phospholipids.

4. The method of claim 3, wherein the mixture of three phospholipids consist of from about 75 to about 87 mole % phosphatidylcholine, about 5 to about 15 mole % phosphatidylethanolamine, and about 3 to about 20 mole % phosphatidylethanolamine-MPEG, wherein MPEG is a PEG group having a terminus methoxy group with a molecular weight in the range of about 2,000 to about 5,000.

5. The method of claim 4, wherein the phospholipids account for about 0.10 to about 7.5 weight percentage of the nanoemulsion.

6. The method of claim 4, wherein the phospholipids account for about 0.10 to about 1.5 weight percentage of the nanoemulsion.

\* \* \* \* \*